US008257365B2

(12) United States Patent  (10) Patent No.: US 8,257,365 B2
Demarais et al.  (45) Date of Patent: Sep. 4, 2012

(54) METHODS AND DEVICES FOR REDUCING HOLLOW ORGAN VOLUME

(75) Inventors: Denise Marie Demarais, Los Gatos, CA (US); James Gannoe, West Milford, NJ (US); Craig Gerbi, Mountain View, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 973 days.

(21) Appl. No.: 11/799,560

(22) Filed: May 2, 2007

(65) Prior Publication Data
US 2007/0208360 A1    Sep. 6, 2007

Related U.S. Application Data

(63) Continuation of application No. 11/056,327, filed on Feb. 11, 2005.

(60) Provisional application No. 60/544,074, filed on Feb. 13, 2004, provisional application No. 60/547,961, filed on Feb. 27, 2004, provisional application No. 60/552,400, filed on Mar. 12, 2004, provisional application No. 60/556,489, filed on Mar. 26, 2004, provisional application No. 60/569,037, filed on May 10, 2004.

(51) Int. Cl.
*A61B 17/12* (2006.01)
*A61B 17/28* (2006.01)
(52) U.S. Cl. .......... 606/139; 606/142; 606/205
(58) Field of Classification Search .......... 606/142, 606/143, 139, 151, 205–209; 227/20, 24, 227/25, 29, 175.1, 176.1
See application file for complete search history.

(56) References Cited

U.S. PATENT DOCUMENTS

| | | | |
|---|---|---|---|
| 2,108,206 A | 2/1938 | Meeker |
| 2,508,690 A | 7/1948 | Schmerl |
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |

(Continued)

FOREIGN PATENT DOCUMENTS
EP    0 137 878 A1    4/1985
(Continued)

OTHER PUBLICATIONS

Benjamin, S.B., et al., *A Double-Blind Cross Over Study of the Garren-Edwards anti-Obesity Bubble*m Abstract Submitted to A/S/ G/E/ 1987, Georgetown University Hospital and Fairfax Hospital, Washington, D.C. and Fairfax, VA.

(Continued)

*Primary Examiner* — Amy Lang
(74) *Attorney, Agent, or Firm* — Nutter McClennen & Fish LLP

(57) ABSTRACT

Methods and devices for providing a minimally-invasive placement of a mechanical structure for reducing the volume of a hollow body organ. Anchors may be secured within the hollow body organ and then cinched together using a tensioning member to form a stricture within the hollow body organ. In another embodiment a tensioning member may be threaded along the hollow body organ and then cinched to reduce the volume. The strictures may be placed anywhere within the hollow body organ, and more than one stricture may be formed within the hollow body organ.

9 Claims, 28 Drawing Sheets

U.S. PATENT DOCUMENTS

| | | |
|---|---|---|
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,696,288 A | 9/1987 | Kuzmak |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,892,244 A | 1/1990 | Fox et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,358,496 A | 10/1994 | Ortiz et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,462,559 A | 10/1995 | Ahmed |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,681,263 A | 10/1997 | Flesch |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |
| 5,888,196 A | 3/1999 | Bonutti |
| 5,897,534 A | 4/1999 | Heim et al. |

| Patent | Kind | Date | Inventors |
|---|---|---|---|
| 5,897,562 | A | 4/1999 | Bolanos et al. |
| 5,904,147 | A | 5/1999 | Conlan et al. |
| 5,906,625 | A | 5/1999 | Bito et al. |
| 5,910,105 | A | 6/1999 | Swain et al. |
| 5,910,149 | A | 6/1999 | Kuzmak |
| 5,921,993 | A | 7/1999 | Yoon |
| 5,927,284 | A | 7/1999 | Borst et al. |
| 5,928,264 | A | 7/1999 | Sugarbaker et al. |
| 5,935,107 | A | 8/1999 | Taylor et al. |
| 5,938,669 | A | 8/1999 | Klaiber et al. |
| 5,947,983 | A | 9/1999 | Solar et al. |
| 5,964,772 | A | 10/1999 | Bolduc et al. |
| 5,964,782 | A | 10/1999 | Lafontaine et al. |
| 5,972,001 | A | 10/1999 | Yoon |
| 5,972,002 | A | 10/1999 | Bark et al. |
| 5,976,161 | A | 11/1999 | Kirsch et al. |
| 5,980,537 | A | 11/1999 | Ouchi |
| 5,993,464 | A | 11/1999 | Knodel |
| 5,993,473 | A | 11/1999 | Chan et al. |
| 6,015,378 | A | 1/2000 | Borst et al. |
| 6,030,364 | A | 2/2000 | Durgin et al. |
| 6,030,392 | A | 2/2000 | Dakov |
| 6,042,538 | A | 3/2000 | Puskas |
| 6,044,847 | A | 4/2000 | Carter et al. |
| 6,067,991 | A | 5/2000 | Forsell |
| 6,074,343 | A | 6/2000 | Nathanson et al. |
| 6,083,241 | A | 7/2000 | Longo et al. |
| 6,086,600 | A | 7/2000 | Kortenbach |
| 6,113,609 | A | 9/2000 | Adams |
| 6,119,913 | A | 9/2000 | Adams et al. |
| 6,120,513 | A | 9/2000 | Bailey et al. |
| 6,136,006 | A | 10/2000 | Johnson et al. |
| 6,159,146 | A | 12/2000 | El Gazayerli |
| 6,159,195 | A | 12/2000 | Ha et al. |
| 6,165,183 | A | 12/2000 | Kuehn et al. |
| 6,179,195 | B1 | 1/2001 | Adams et al. |
| 6,186,942 | B1 | 2/2001 | Sullivan et al. |
| 6,186,985 | B1 | 2/2001 | Snow |
| 6,197,022 | B1 | 3/2001 | Baker |
| 6,200,318 | B1 | 3/2001 | Har-Shai et al. |
| 6,206,822 | B1 | 3/2001 | Foley et al. |
| 6,206,893 | B1 | 3/2001 | Klein et al. |
| 6,224,614 | B1 | 5/2001 | Yoon |
| 6,231,561 | B1 | 5/2001 | Frazier et al. |
| 6,248,058 | B1 | 6/2001 | Silverman et al. |
| 6,254,642 | B1 | 7/2001 | Taylor |
| 6,273,897 | B1 | 8/2001 | Dalessandro et al. |
| 6,279,809 | B1 | 8/2001 | Nicolo |
| 6,290,674 | B1 | 9/2001 | Roue et al. |
| 6,293,923 | B1 | 9/2001 | Yachia et al. |
| 6,302,917 | B1 | 10/2001 | Dua et al. |
| 6,312,437 | B1 | 11/2001 | Kortenbach |
| 6,328,689 | B1 | 12/2001 | Gonzalez et al. |
| 6,334,865 | B1 | 1/2002 | Redmond et al. |
| 6,338,345 | B1 | 1/2002 | Johnson et al. |
| 6,352,543 | B1 | 3/2002 | Cole |
| 6,358,197 | B1 | 3/2002 | Silverman et al. |
| 6,379,366 | B1 | 4/2002 | Fleischmann et al. |
| 6,387,104 | B1 | 5/2002 | Pugsley, Jr. et al. |
| 6,398,795 | B1 | 6/2002 | McAlister et al. |
| 6,416,535 | B1 | 7/2002 | Lazarus |
| 6,423,087 | B1 | 7/2002 | Sawada |
| 6,432,040 | B1 | 8/2002 | Meah |
| 6,447,533 | B1 | 9/2002 | Adams |
| 6,460,543 | B1 | 10/2002 | Forsell |
| 6,461,366 | B1 | 10/2002 | Seguin |
| 6,475,136 | B1 | 11/2002 | Forsell |
| 6,491,707 | B2 | 12/2002 | Makower et al. |
| 6,494,888 | B1 | 12/2002 | Laufer et al. |
| 6,506,196 | B1 | 1/2003 | Laufer |
| 6,535,764 | B2 | 3/2003 | Imran et al. |
| 6,540,789 | B1 | 4/2003 | Silverman et al. |
| 6,551,310 | B1 | 4/2003 | Ganz et al. |
| 6,554,844 | B2 | 4/2003 | Lee et al. |
| 6,558,400 | B2 | 5/2003 | Deem et al. |
| 6,561,969 | B2 | 5/2003 | Frazier et al. |
| 6,572,629 | B2 | 6/2003 | Kalloo et al. |
| 6,579,301 | B1 | 6/2003 | Bales et al. |
| 6,592,596 | B1 | 7/2003 | Geitz |
| 6,605,037 | B1 | 8/2003 | Moll et al. |
| 6,626,899 | B2 | 9/2003 | Houser et al. |
| 6,632,227 | B2 | 10/2003 | Adams |
| 6,656,194 | B1 | 12/2003 | Gannoe et al. |
| 6,663,598 | B1 | 12/2003 | Carrillo, Jr. et al. |
| 6,663,639 | B1 | 12/2003 | Laufer et al. |
| 6,663,640 | B2 | 12/2003 | Kortenbach |
| 6,675,809 | B2 | 1/2004 | Stack et al. |
| 6,682,520 | B2 | 1/2004 | Ingenito |
| 6,689,062 | B1 | 2/2004 | Mesallum |
| 6,692,485 | B1 | 2/2004 | Brock et al. |
| 6,716,222 | B2 | 4/2004 | McAlister et al. |
| 6,733,512 | B2 | 5/2004 | McGhan |
| 6,736,822 | B2 | 5/2004 | McClellan et al. |
| 6,740,098 | B2 | 5/2004 | Abrams et al. |
| 6,740,121 | B2 | 5/2004 | Geitz |
| 6,746,460 | B2 | 6/2004 | Gannoe et al. |
| 6,746,489 | B2 | 6/2004 | Dua et al. |
| 6,754,536 | B2 | 6/2004 | Swoyer et al. |
| 6,755,849 | B1 | 6/2004 | Gowda et al. |
| 6,755,869 | B2 | 6/2004 | Geitz |
| 6,756,364 | B2 | 6/2004 | Barbier et al. |
| 6,764,518 | B2 | 7/2004 | Godin |
| 6,773,440 | B2 | 8/2004 | Gannoe et al. |
| 6,773,441 | B1 | 8/2004 | Laufer et al. |
| 6,786,898 | B2 | 9/2004 | Guenst |
| 6,790,214 | B2 | 9/2004 | Kraemer et al. |
| 6,802,868 | B2 | 10/2004 | Silverman et al. |
| 6,821,285 | B2 | 11/2004 | Laufer et al. |
| 6,830,546 | B1 | 12/2004 | Chin et al. |
| 6,835,199 | B2 | 12/2004 | McGuckin, Jr. et al. |
| 6,835,200 | B2 | 12/2004 | Laufer et al. |
| 6,837,848 | B2 | 1/2005 | Bonner et al. |
| 6,840,423 | B2 | 1/2005 | Adams et al. |
| 6,845,776 | B2 | 1/2005 | Stack et al. |
| 6,896,682 | B1 | 5/2005 | McClellan et al. |
| 6,916,332 | B2 | 7/2005 | Adams |
| 6,926,722 | B2 | 8/2005 | Geitz |
| 6,966,919 | B2 | 11/2005 | Sixto, Jr. et al. |
| 6,981,978 | B2 | 1/2006 | Gannoe |
| 6,991,643 | B2 | 1/2006 | Saadat |
| 6,994,715 | B2 | 2/2006 | Gannoe et al. |
| 7,020,531 | B1 | 3/2006 | Colliou et al. |
| 7,025,791 | B2 | 4/2006 | Levine et al. |
| 7,033,373 | B2 | 4/2006 | de al Torre et al. |
| 7,033,378 | B2 | 4/2006 | Smith et al. |
| 7,033,384 | B2 | 4/2006 | Gannoe et al. |
| 7,037,343 | B2 | 5/2006 | Imran |
| 7,037,344 | B2 | 5/2006 | Kagan et al. |
| 7,059,510 | B2 | 6/2006 | Orban, III |
| 7,063,715 | B2 | 6/2006 | Onuki et al. |
| 7,083,629 | B2 | 8/2006 | Weller et al. |
| 7,083,630 | B2 | 8/2006 | DeVries et al. |
| 7,087,011 | B2 | 8/2006 | Cabiri et al. |
| 7,097,650 | B2 | 8/2006 | Weller et al. |
| 7,160,312 | B2 | 1/2007 | Saadat |
| 7,520,884 | B2 | 4/2009 | Swanstrom et al. |
| 7,666,195 | B2 * | 2/2010 | Kelleher et al. ................ 606/144 |
| 2001/0014800 | A1 | 8/2001 | Frazier et al. |
| 2001/0020190 | A1 | 9/2001 | Taylor |
| 2001/0037127 | A1 | 11/2001 | De Hoyos Garza |
| 2002/0022851 | A1 | 2/2002 | Kalloo et al. |
| 2002/0035361 | A1 | 3/2002 | Houser et al. |
| 2002/0040226 | A1 | 4/2002 | Laufer et al. |
| 2002/0047036 | A1 | 4/2002 | Sullivan et al. |
| 2002/0058967 | A1 | 5/2002 | Jervis |
| 2002/0072761 | A1 | 6/2002 | Abrams et al. |
| 2002/0077661 | A1 | 6/2002 | Saadat |
| 2002/0078967 | A1 | 6/2002 | Sixto, Jr. et al. |
| 2002/0082621 | A1 | 6/2002 | Schurr et al. |
| 2002/0143346 | A1 | 10/2002 | McGuckin, Jr. et al. |
| 2002/0165589 | A1 | 11/2002 | Imran et al. |
| 2002/0183765 | A1 * | 12/2002 | Adams ......................... 606/139 |
| 2002/0183768 | A1 | 12/2002 | Deem et al. |
| 2002/0193816 | A1 | 12/2002 | Laufer et al. |
| 2003/0040804 | A1 | 2/2003 | Stack et al. |
| 2003/0040808 | A1 | 2/2003 | Stack et al. |
| 2003/0065340 | A1 | 4/2003 | Geitz |
| 2003/0065359 | A1 | 4/2003 | Weller et al. |

| | | |
|---|---|---|
| 2003/0093117 A1* | 5/2003 | Saadat .................. 606/221 |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1* | 9/2003 | Gambale .................. 606/139 |
| 2003/0208209 A1 | 11/2003 | Gambale et al. |
| 2003/0216754 A1 | 11/2003 | Kraemer et al. |
| 2003/0225312 A1 | 12/2003 | Suzuki et al. |
| 2004/0006351 A1* | 1/2004 | Gannoe et al. ............ 606/139 |
| 2004/0009224 A1 | 1/2004 | Miller |
| 2004/0010271 A1 | 1/2004 | Kortenbach |
| 2004/0024386 A1 | 2/2004 | Deem et al. |
| 2004/0030347 A1 | 2/2004 | Gannoe et al. |
| 2004/0034371 A1 | 2/2004 | Lehman et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0210243 A1 | 10/2004 | Gannoe et al. |
| 2004/0215180 A1 | 10/2004 | Starkebaum et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0021681 A1 | 1/2005 | Oommen |
| 2005/0027307 A1* | 2/2005 | Schwartz et al. ............ 606/151 |
| 2005/0033328 A1 | 2/2005 | Laufer et al. |
| 2005/0038415 A1 | 2/2005 | Rohr et al. |
| 2005/0038462 A1 | 2/2005 | Lubock et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0247320 A1 | 11/2005 | Stack et al. |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |
| 2007/0208360 A1 | 9/2007 | Demarais et al. |
| 2007/0213740 A1 | 9/2007 | Deem et al. |
| 2007/0213748 A1 | 9/2007 | Deem et al. |
| 2007/0219570 A1 | 9/2007 | Deem et al. |
| 2007/0233161 A1 | 10/2007 | Weller et al. |
| 2007/0233162 A1 | 10/2007 | Gannoe et al. |
| 2007/0250083 A1 | 10/2007 | Deem et al. |
| 2007/0282349 A1 | 12/2007 | Deem et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| FR | 2768324 A1 | 3/1999 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO-0007640 A2 | 2/2000 |
| WO | WO 00/32137 A1 | 6/2000 |
| WO | WO 00/39708 A1 | 7/2000 |
| WO | WO 00/48656 A1 | 8/2000 |
| WO | WO 00/78227 A1 | 12/2000 |
| WO | WO 00/78229 A1 | 12/2000 |
| WO | WO-0126557 A1 | 4/2001 |
| WO | WO-0128432 A1 | 4/2001 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO-0239880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A1 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |

| | | |
|---|---|---|
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO-2004/019788 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Büchler, M.W., M.D. et al., A Technique for Gastroplasty As a Substitute for the Esophagus: Fundus Rotation Gastroplasty, *Journal of the American College of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D.[1], et al.. Gastro-Clip® Gastroplasty: A Very Long-Term Complication, *Obesity Surgery*, 14, © FD-Communications Inc.. 2004.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Endo Gia* Universal, Single UseStapler and Endo GIA Roticulator*, Brochure, 8 pages, Undated.

Filipi, Charles J. M.D., et al., Transoral, Flexible Endoscopic Suturing for Treatment of GERD: A Multicenter Trial, *Gastrointestinal Endoscopy*,. vol. 53, No. 4, pp. 416-422, 2001.

Gray, Henry, R.R.S., *Anatomy of the Human Body*, The Digestive System, Thirtieth American Edition, pp. 1466-1467 (Undated).

Guidant, Internet, AXIUS™ VACUUM 2 Stabilizer Systems, Internet Website—www.guidant.com/products/axius_vacuum.shtml, 8 pages, visited May 27, 2003.

Gukovsky-Reicher, S., M.D. et al., Expandable Metal Esophageal Stents: Efficacy and Safety. Review of Current Literature Data and of 53 Stents Placed at Harbor-UCLA Medical Center, www.medscape.com/viewarticle/423508_print pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device for Transanal Endoscopic Microsurgery, *Blackwell Science Ltd*. p. 1290, 1997.

Johnson & Johnson Gateway[SM] Endopath 3mm, 5mm and 10 mm Diameter Endoscopic Instruments, Internet Website—www.inigateway.com/home.ihtml?loc=USENG&page=viewContent&parentId-0900 . . . , 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor (class 1, 878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Edoscopy*, vol. 32, No. 1 pp. 36-38 1986.

Swain, C. Paul, M.D., Endoscopic Sewing and Stapling Machines, *Endoscopy* pp. 205-210, © Georg Thieme Verlag Stuttgart, New York, 1997.

Swain, C. Paul, M.D. et al., An Endoscopic Stapling Device: The Development of a New Flexible Endoscopically Controlled Device for Placing Multiple Transmural Staples in Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

U.S. Appl. No. 10/773,883, filed Feb. 5, 2004 unpublished; Inventors: Gerbi et al.

U.S. Appl. No. 10/797,439, filed Mar. 9, 2004 unpublished; Inventors: Weller et al.

* cited by examiner

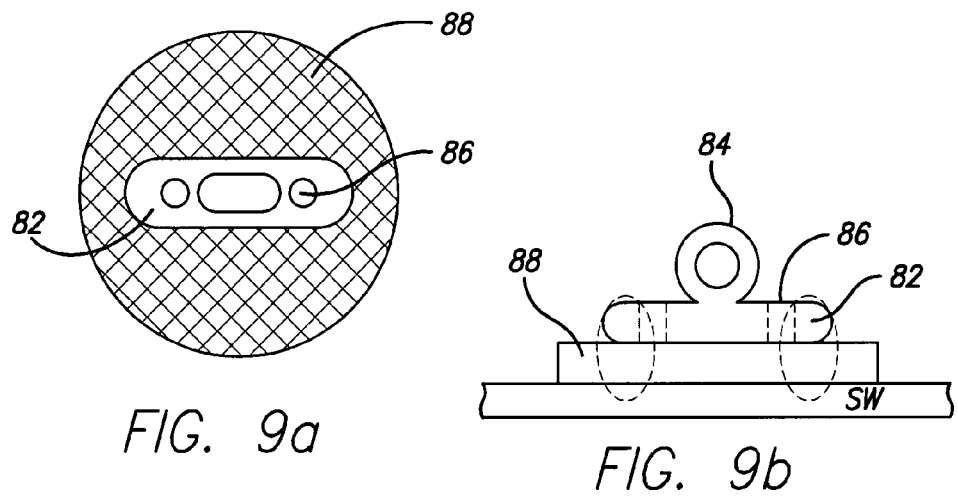
FIG. 9a    FIG. 9b
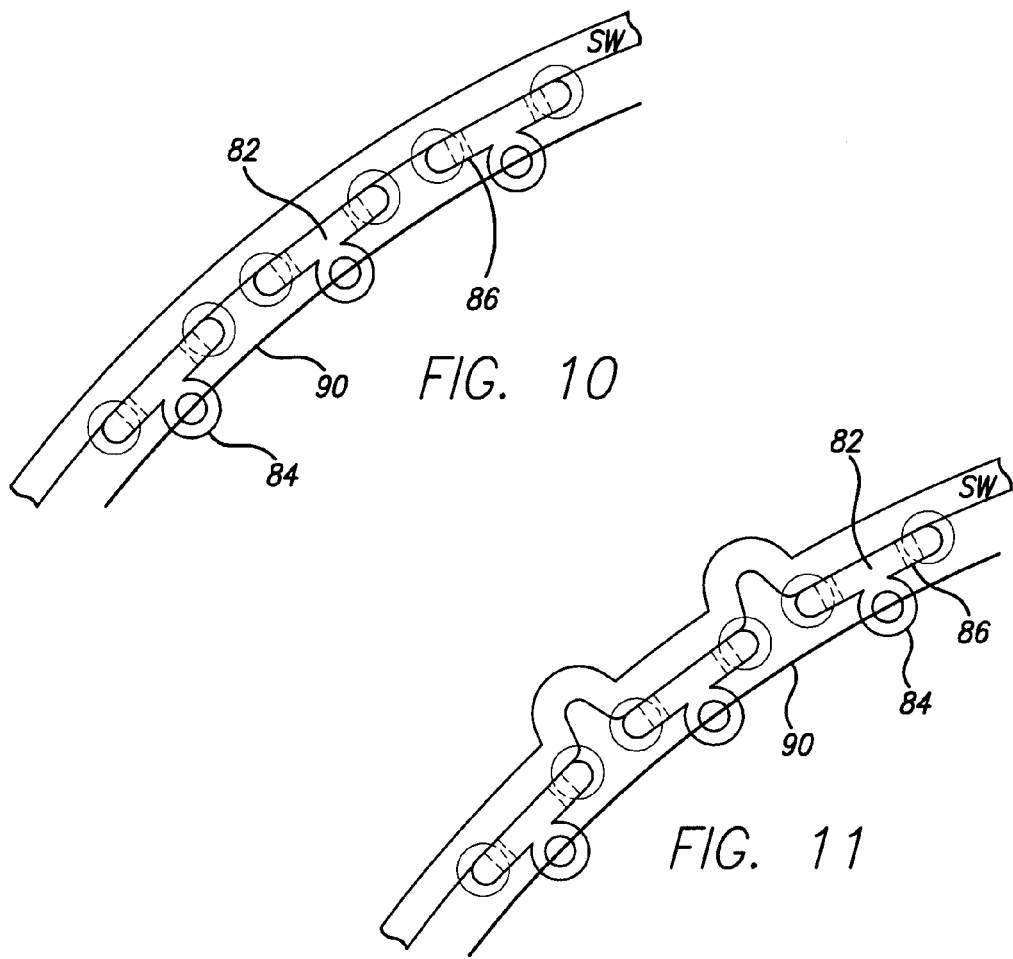
FIG. 10
FIG. 11

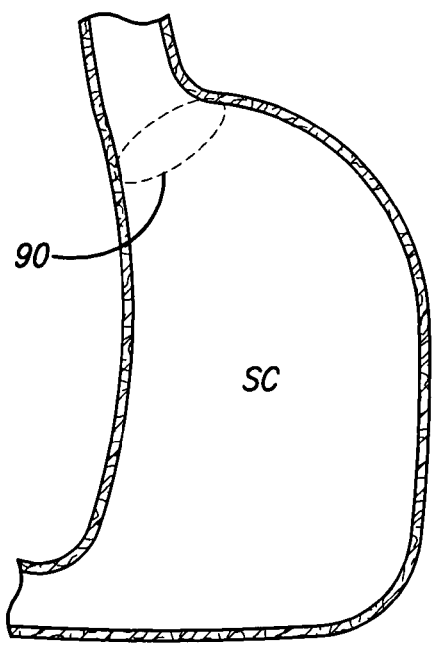 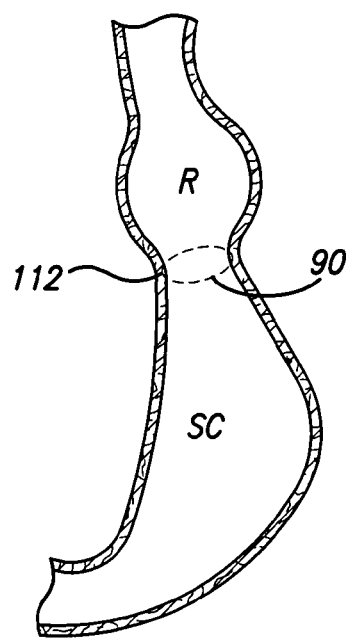
FIG. 15a   FIG. 15b
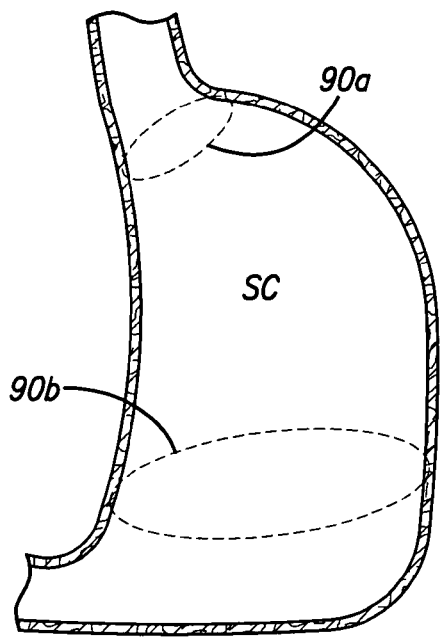 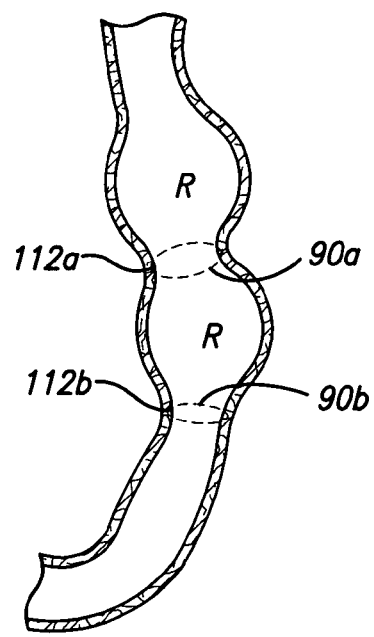
FIG. 16a   FIG. 16b

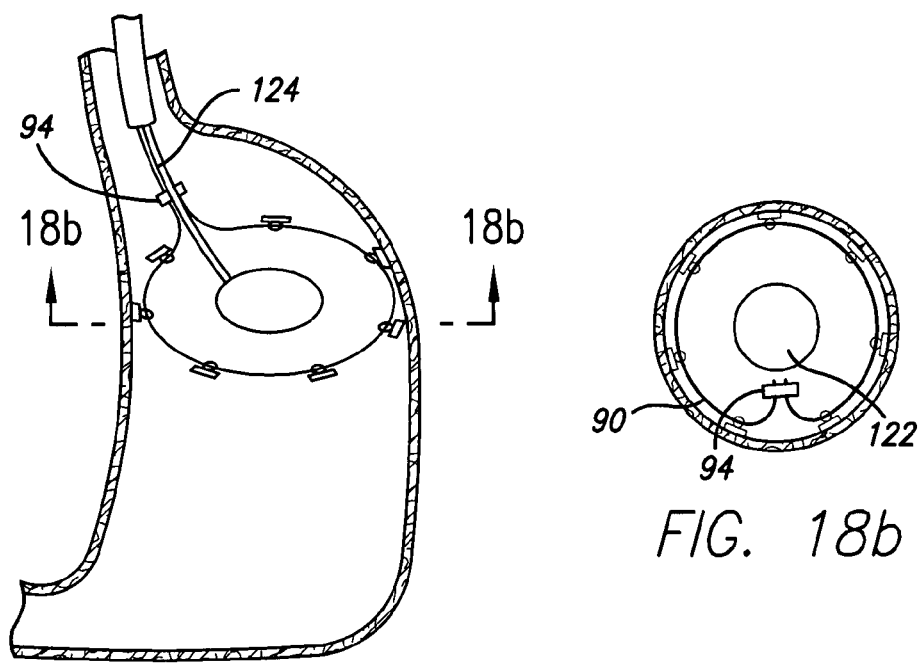
FIG. 18a
FIG. 18b
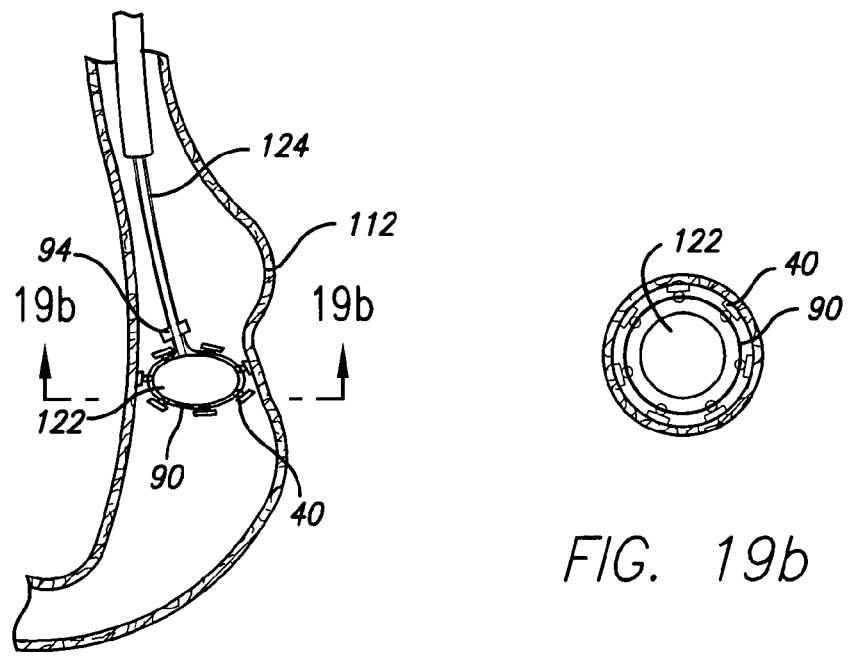
FIG. 19a
FIG. 19b

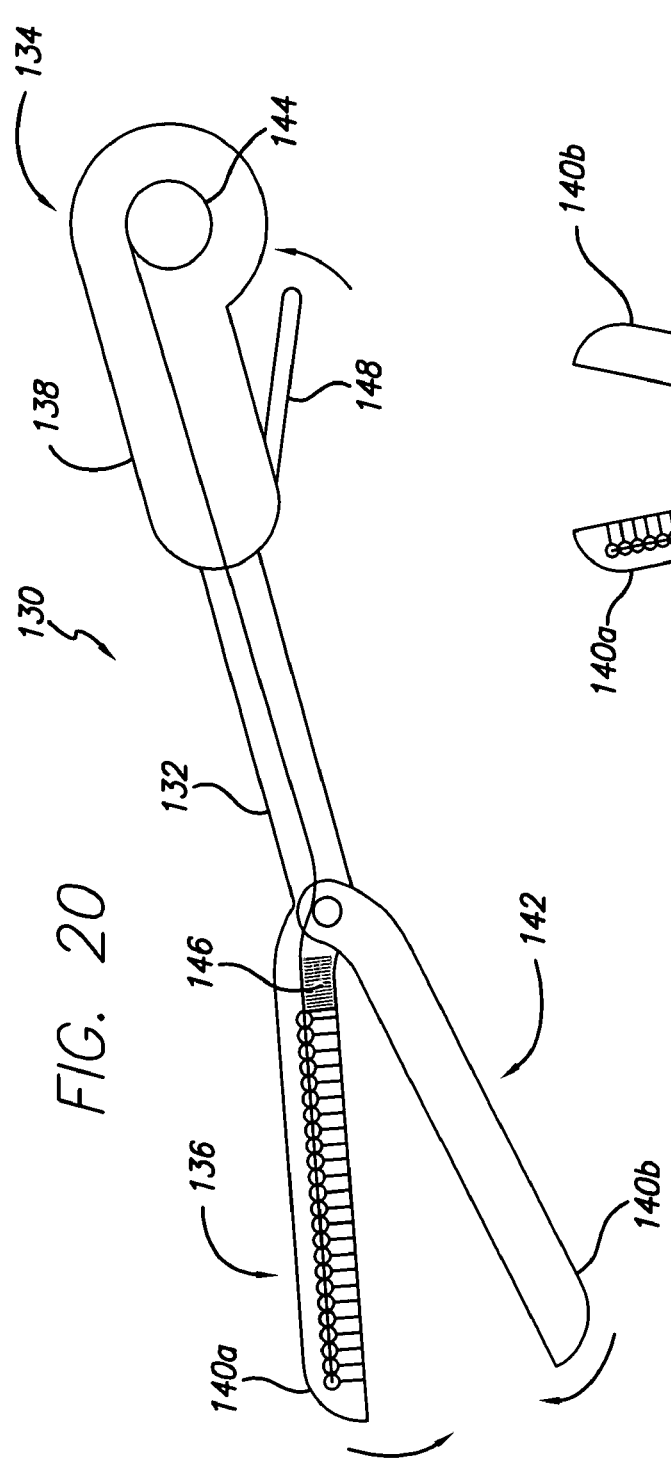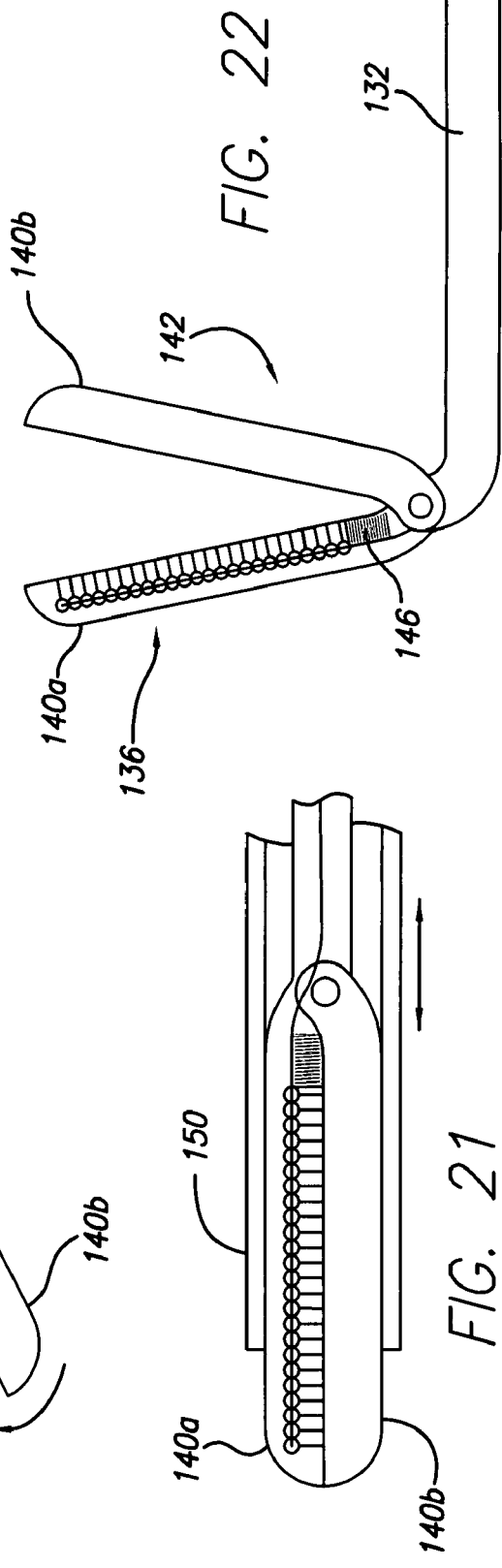

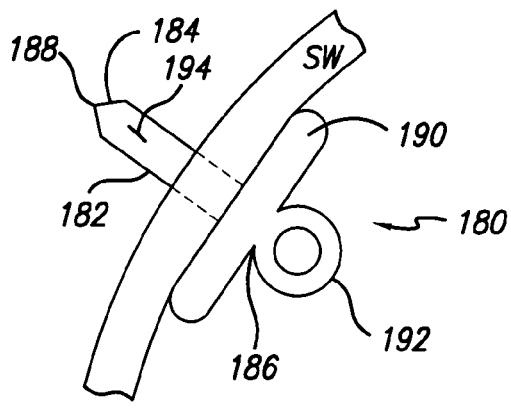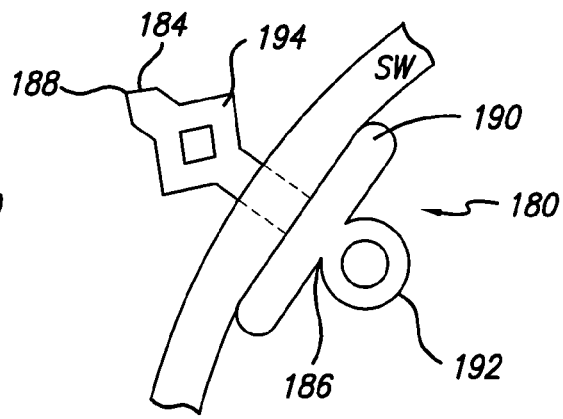
FIG. 23a  FIG. 23b
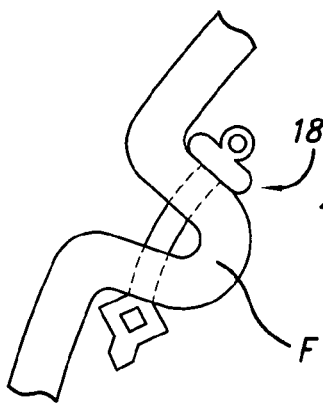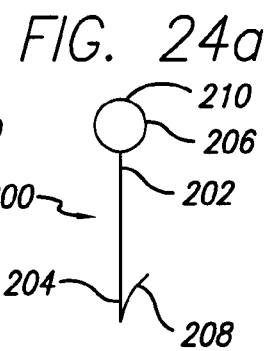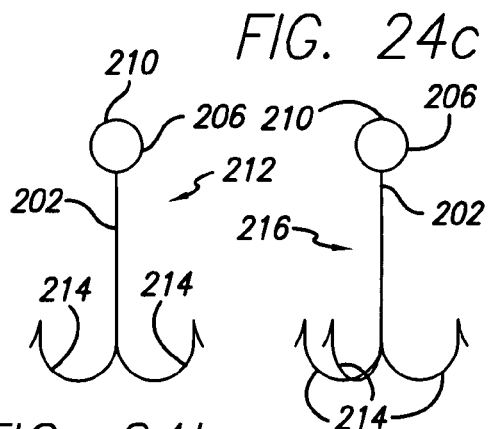
FIG. 23c  FIG. 24b
FIG. 24a  FIG. 24c
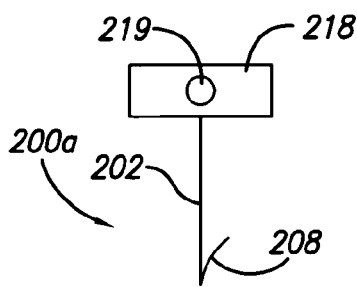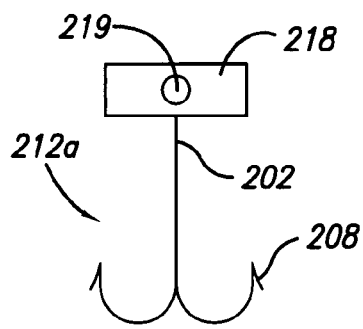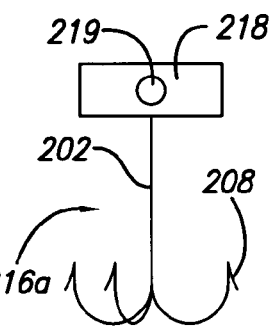
FIG. 24d  FIG. 24e  FIG. 24f

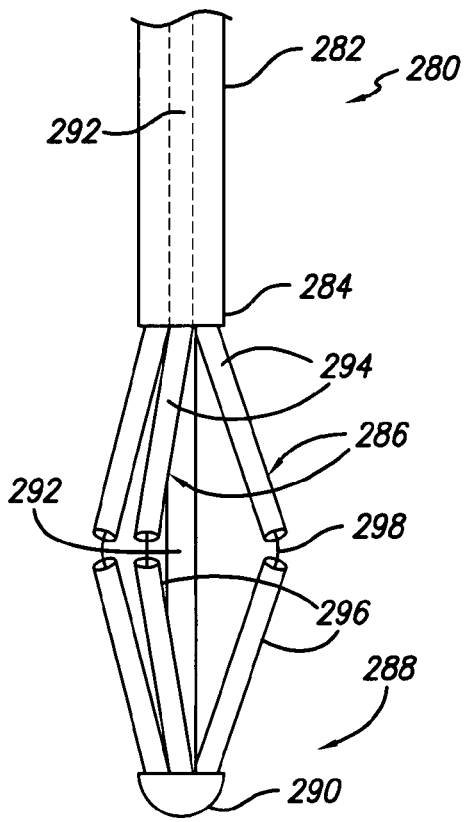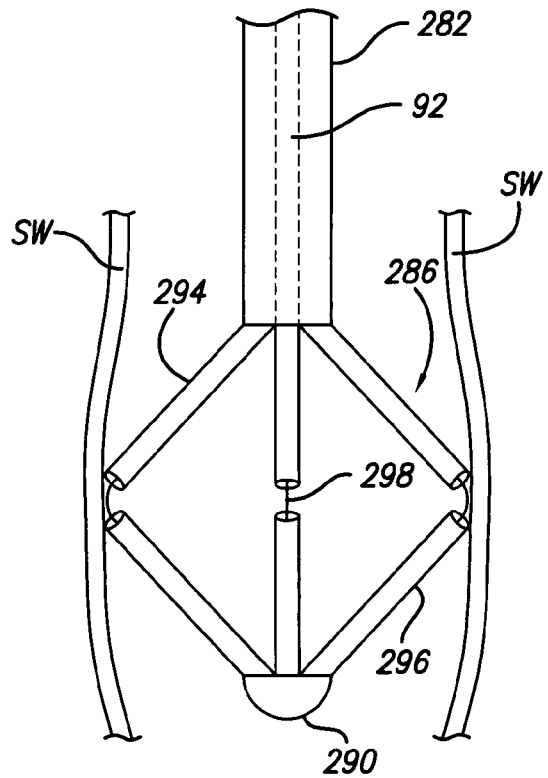
FIG. 30
FIG. 31
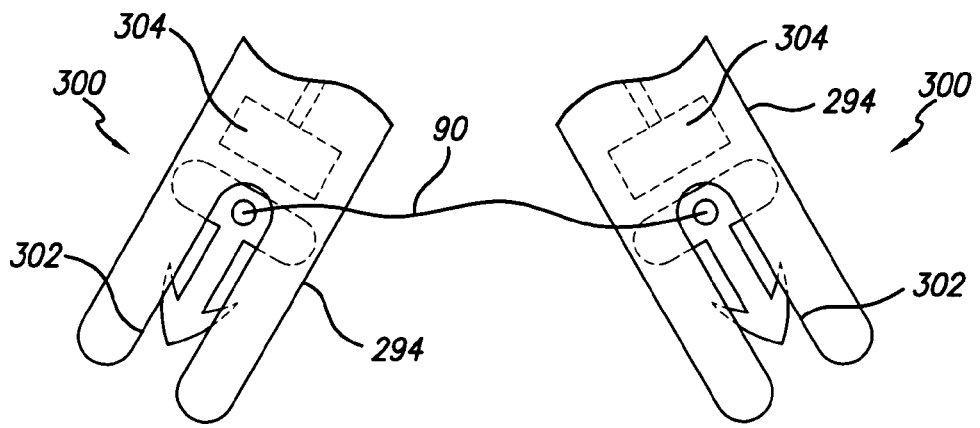
FIG. 32

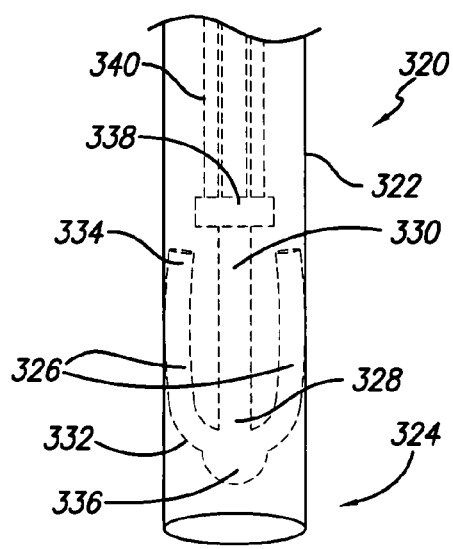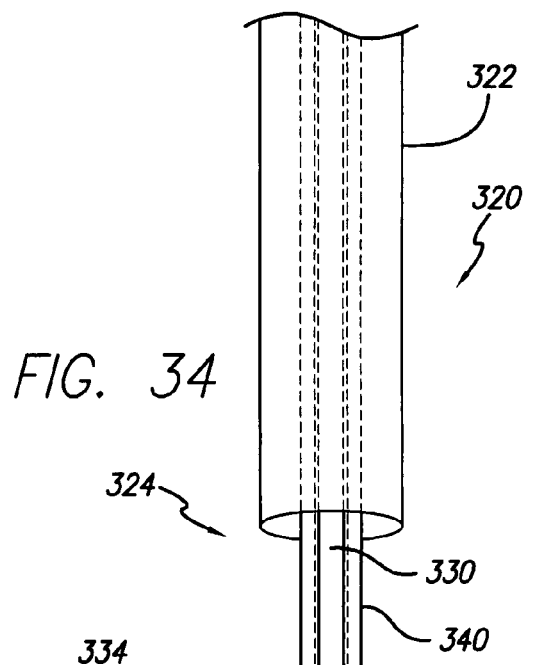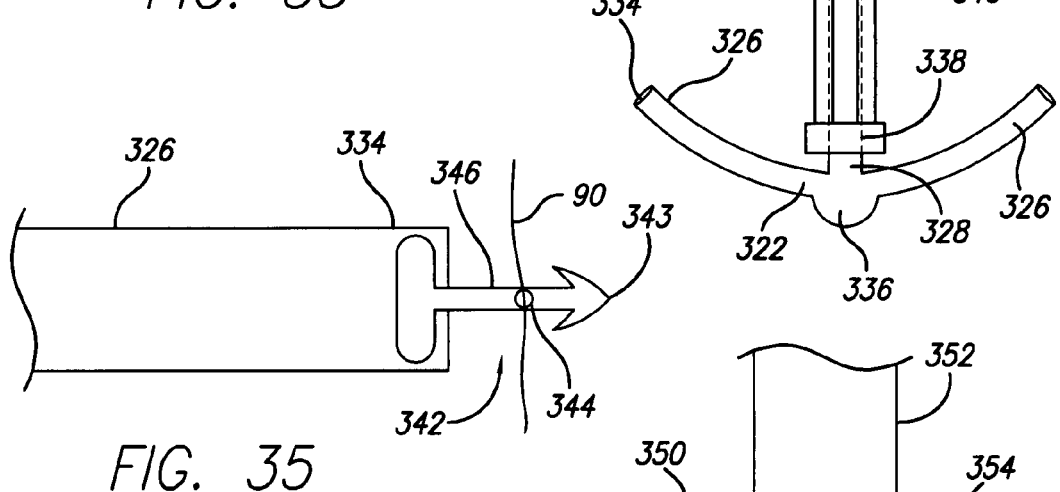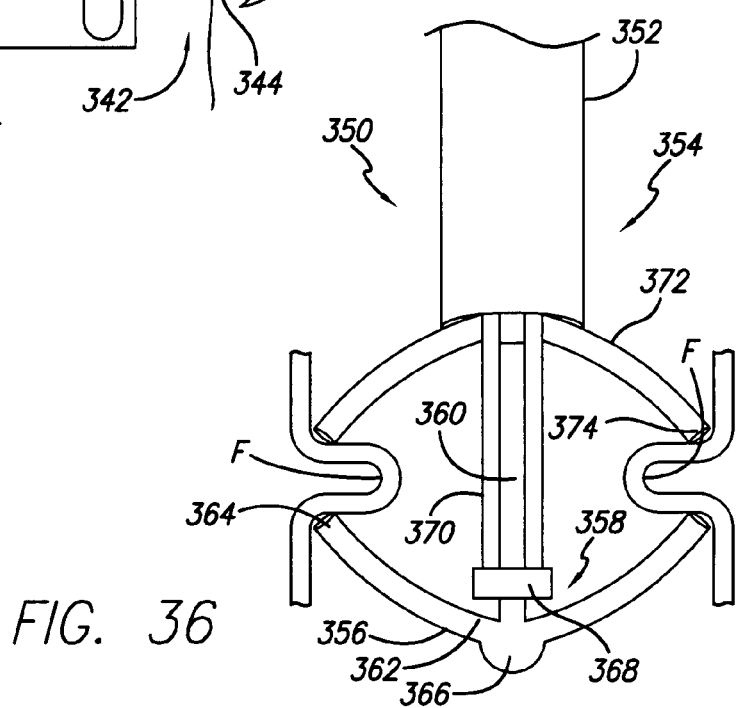
FIG. 33
FIG. 34
FIG. 35
FIG. 36

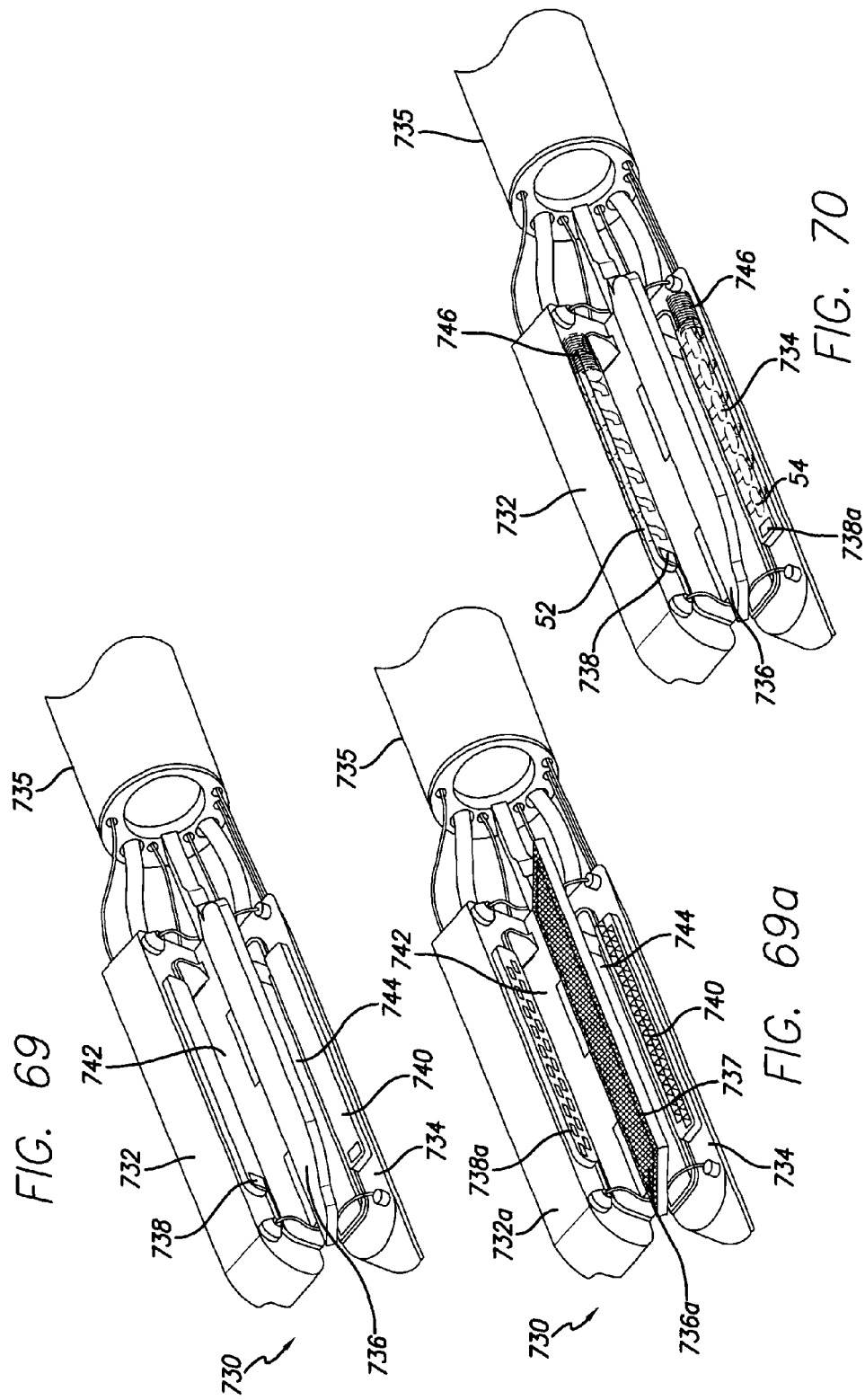

METHODS AND DEVICES FOR REDUCING HOLLOW ORGAN VOLUME

CROSS-REFERENCE TO RELATED APPLICATION

This continuation application is claiming priority to the following co-pending application Ser. No. 11/056,327 filed Feb. 11, 2005, which claims priority to applications: U.S. Ser. No. 60/544,074 filed Feb. 13, 2004; U.S. Ser. No. 60/547,961 filed Feb. 27, 2004; U.S. Ser. No. 60/552,400 filed Mar. 12, 2004; U.S. Ser. No. 60/556,489 filed Mar. 26, 2004; and U.S. Ser. No. 60/569,037 filed May 10, 2004, the entire contents of each are incorporated herein by reference.

BACKGROUND OF THE INVENTION

1. Field of the Invention

The present invention pertains to medical equipment and more particularly to mechanical methods for reducing the volume of the stomach for the treatment of obesity.

2. General Background and State of the Art

Approximately 64% of Americans are overweight and obesity is rapidly becoming an epidemic resulting in a multitude of co-morbidities (e.g. cardiovascular disease, diabetes, etc.) and enormous medical costs. Approximately $75 billion dollars are spent each year on weight-related diseases in the US alone.

Historically, methods of weight reduction have ranged from oral pharmacological means, a multitude of diets, and various exercise programs. These approaches have generally resulted in temporary weight loss, with no or limited long-term benefit.

In recent years, the concept of obesity being a disease has gained momentum. To that end, surgical treatments have been developed to provide a more permanent solution (e.g. stomach stapling, gastric bypass, and the like). However, these treatments are generally surgical in nature, which imply inherent risk and high cost to the patient.

Thus, it remains desirable to develop new alternatives to provide non-invasive or minimally-invasive solutions to obesity.

SUMMARY OF THE INVENTION

The present invention overcomes some or all of the shortcomings of the current techniques by providing a minimally-invasive placement of a mechanical structure for reducing the volume of the stomach via an esophageal approach.

One embodiment involves esophageal delivery of a series of anchors into the stomach wall. The anchors are connected with a tensioning member (e.g. suture), which is subsequently tensioned to cinch the anchors together, resulting in a stricture (or stoma) and reduction in stomach volume. Once the desired size-reduction is achieved, the delivery device secures the tensioning member and disconnects it. The delivery system is designed to hold multiple anchors, which are placed around a circumference of the stomach using endoscopic guidance. In one embodiment, a standard endoscope is attached to the delivery system, but an endoscope may also be integrated into the delivery system. In an alternative embodiment, the delivery system is compatible with the working lumen of a standard endoscope. The anchors may be constructed from stainless steel, shape-memory alloys, or various polymers and are attached to the stomach wall via sutures, various crimping techniques (e.g. staples), rivets, grommets, or the like and have eyelets through which the tensioning member is strung. The first anchor may be fixedly attached to the tensioning member and the others may be free floating on the tensioning member. The tensioning member is sufficiently flexible to allow for cinching the anchors together and is constructed from a high-tensile, corrosion-resistant material (e.g. Kevlar fiber, braid or cable; stainless steel wire, braid or cable). The above procedure may be performed more than once to create multiple strictures and achieve the desired volume reduction.

An alternative embodiment involves esophageal delivery of a tensioning member, which is a suture or the like stitched to the stomach wall in a circumferential manner. Multiple stitches are placed under endoscopic guidance (integral or non-integral) to define a circumference and a cinching device is utilized to apply tension the tensioning member, resulting in a volume reduction. As used herein, integral means formed together as a unit, and non-integral means functioning as separate units. The cinching device is then used to secure the tensioning member (e.g. a knot) and disconnect it. This procedure may also be performed more than one to create multiple strictures in the stomach.

In another embodiment, the delivery system deploys the anchors and tensioning member, and a subsequent device is utilized to tension (i.e., cinch), secure, and terminate the tensioning member.

A calibration mechanism may also be designed into the system to control the size of the stricture to be created. The mechanism may take the form of a non-compliant or semi-compliant balloon, which may be inflated to a desired diameter. The mechanism may also be comprised of a mechanically-expanding device. The calibration mechanism may also be simply a semi-rigid rod or tube, and the delivery system itself may act as the calibration member. The tensioning member may then be tensioned until it contacts the calibration device, and then the tensioning member may be secured and terminated as described above.

It may also be desirable to adjust the size of the stricture post-procedure. The preferred method for adjusting the stricture size could be to allow for the termination of the tensioning member (e.g. suture) to be mechanical in nature (rather than a knot) and allow for additional suture to be available for loosening the stricture. The suture could be on a spool or other system such that the suture could also be tightened. Alternatively, the original tensioning member could be severed and removed, and an accessory device may be provided to restring the anchors back together to achieve an alternative constriction in the stomach.

Multiple devices may be used to optimally place these anchors and tensioning member, apply tension to cinch the stomach wall together, secure the tensioning member, terminate the tensioning member, and visualize the procedure.

An alternative device for reducing stomach volume is a diaphragm deployed within a region of the stomach to divide the stomach into smaller sections. In one embodiment the diaphragm is placed in a near-vertical orientation to the esophagus and extends (approximately) perpendicularly to the esophagus until it contacts the distal portion of the stomach. Alternatively, the diaphragm could be placed nearly perpendicularly to the esophagus or at an angle, such that the food passageway cross-sectional area is reduced over a discrete length. These diaphragms would be anchored to the stomach wall via previously-described anchoring techniques, and a tensioning mechanism is provided to tighten or stiffen the diaphragm to create a wall.

Another method for reducing stomach volume is to attach a series of anchors to the stomach wall using adhesive. The anchors have one or more eyelets, through which a tensioning member is strung. Once the anchors are fixed to the stomach wall, the tensioning member is tensioned and constrained. In this manner, the wall of the stomach is not punctured or otherwise damaged and a large anchor surface area may be achieved. The adhesive may be incorporated into the anchor itself or applied via a delivery system. The anchors may also be adhered between two folds of tissue, such that the anchor is sandwiched between the tissue. This may create a more durable bond and may promote tissue in-growth.

BRIEF DESCRIPTION OF THE DRAWINGS

FIGS. 9a and 9b depict the anchor of FIG. 7 attached to a flexible material.

FIG. 10 depicts partial view of a plurality of anchors attached to the stomach wall and an un-tensioned tensioning member attached to the anchors.

FIG. 11 depicts a partial view of the anchors attached to the stomach wall of FIG. 10 with the tensioning member tensioned to cinch the anchors together.

FIG. 15a depicts a schematic view of a stomach cavity with a tensioning member secured to the inner stomach wall.

FIG. 15b depicts a schematic view of the tensioning member of FIG. 15a forming a stricture within the stomach cavity.

FIG. 16a depicts a schematic view of a stomach cavity with a first and a second tensioning member secured to the inner stomach wall.

FIG. 16b depicts a schematic view of the first and second tensioning members of FIG. 16a forming a first and a second stricture within the stomach cavity.

FIG. 18a depicts a schematic view of a balloon inflated in the stomach cavity with a tensioning member anchored to the inner stomach wall FIG. 18b depicts a cross-sectional view taken along line 18b-18b of FIG. 18a.

FIG. 19a depicts a schematic view of the tensioning member of FIG. 18a tensioned around the inflated balloon.

FIG. 19b depicts a cross-sectional view taken along line 19b-19b of FIG. 19a.

FIG. 20 depicts a device for securing staples to the stomach wall.

FIG. 21 depicts a distal end of a device being actuated with a sheath.

FIG. 22 depicts another embodiment of the device shown in FIG. 20.

FIG. 23a depicts an anchor piercing the stomach wall.

FIGS. 23b and 23c depict the anchor of FIG. 23a in a locked configuration.

FIGS. 24a through 24f depict embodiments of a hook anchor.

FIGS. 30 through 32 depict a device for securing anchors to the stomach wall.

FIGS. 33 through 35 depict a another device for securing anchors to the stomach wall.

FIG. 36 depicts yet another device for securing anchors to the stomach wall.

FIG. 69 depicts yet another device for delivering anchors to a fold of tissue.

FIG. 69*a* depicts an alternative embodiment of the device depicted in FIG. 69.

FIG. 70 depicts another alternative embodiment of the device depicted in FIG. 69.

DETAILED DESCRIPTION OF THE PREFERRED EMBODIMENTS

As will be discussed in detail below, a method of reducing the volume of the stomach involves creating strictures or stomas within the stomach cavity. These strictures can be created through minimally-invasive placement of a mechanical structure for reducing the volume of the stomach via an esophageal approach. For ease of reference, the following embodiments will be described as being advanced transorally to the stomach, although the embodiments of the restricting devices can be used within other hollow body organs as well.

Figure 1:
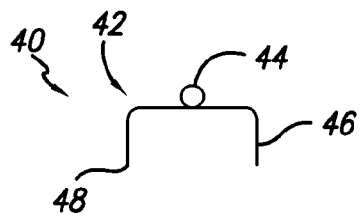
FIG. 1 depicts a staple.
Figure 2A:
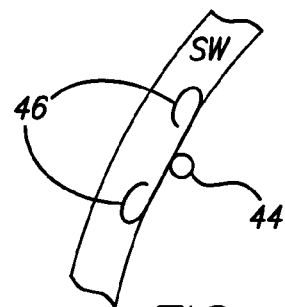
FIGS. 2a and 2b depict the staple of FIG. 1 attached to the stomach wall.
Figure 2B:
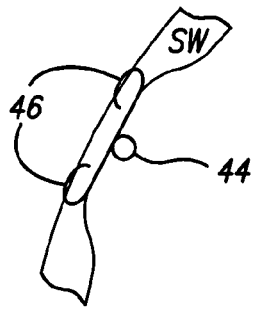

One embodiment for reducing the volume of the stomach cavity includes placing anchors along the stomach lining in a desired pattern, and then cinching the anchors together with a tensioning member, such as a suture or wire. FIGS. 1-2*b* show an embodiment of an anchor 40 that may be used in the trans-esophageal or trans-oral procedure. The anchor in this embodiment is a staple 42 having an eyelet 44 and arms 46, each with a sharp tip 48. FIG. 1 shows the staple in an open configuration with the arms being relatively straight and parallel to one another. In use, the staple is delivered to the stomach cavity in the open configuration and then stapled so that the staple is attached to the stomach wall SW in a closed configuration as shown in FIGS. 2*a* and 2*b*. In the closed configuration the arms of the staple are bent towards one another, each being formed into a hook-like shape. The staple may or may not puncture through all layers of the stomach wall. FIG. 2*a* depicts the staple attached to the stomach wall so that the arms of the staple have not punctured through the stomach wall and the eyelet of the staple positioned along the inner stomach wall within the stomach cavity SC. FIG. 2*b* shows the staple attached to the stomach wall with the arms of the staple having punctured through all layers the stomach wall.

Figure 3A:
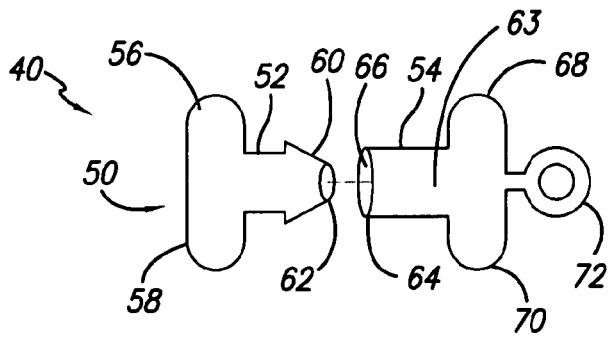
FIGS. 3a and 3b depict a rivet.
Figure 3B:
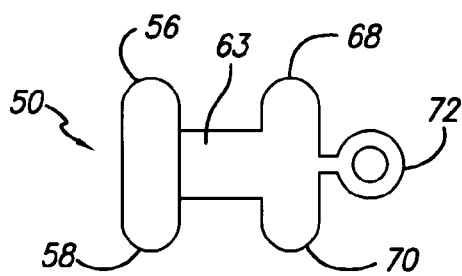
Figure 3C:
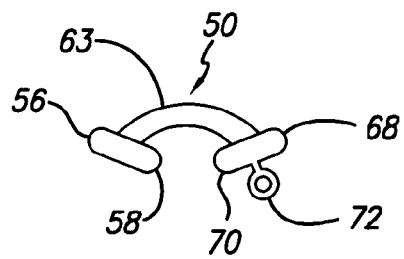
Figure 4A:
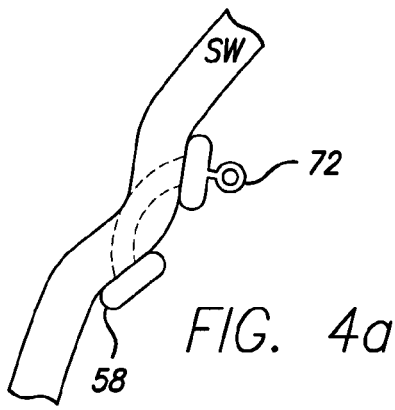
FIGS. 4a and 4b depict the rivet of FIGS. 3a and 3b attached to the stomach wall.
Figure 4B:
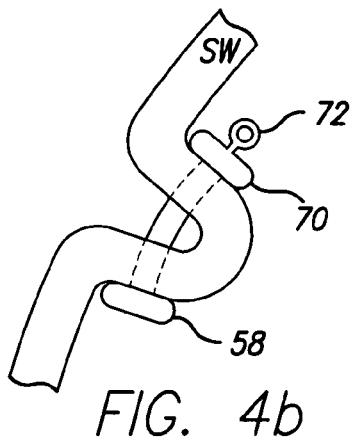
Figure 5A:
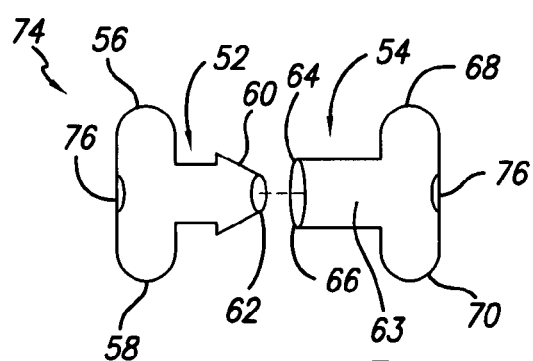
FIGS. 5a and 5b depict another embodiment of a rivet.
Figure 5B:
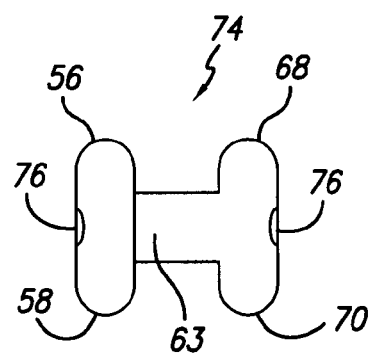
Figure 6A:
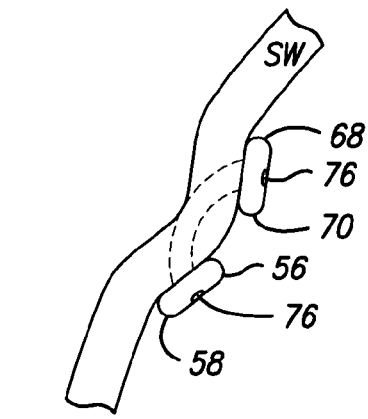
FIGS. 6a and 6b depict the rivet of FIGS. 5a and 5b attached to the stomach wall.
Figure 6B:
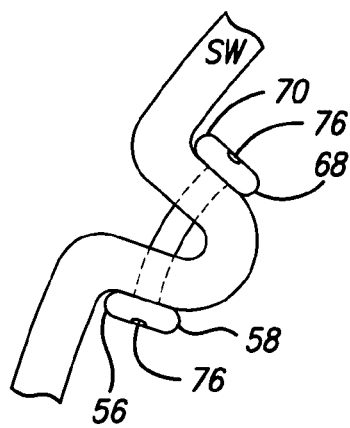

Another embodiment of the anchor 40 is shown in FIGS. 3*a* through 4*b*. Referring to FIG. 3*a*, the anchor is a rivet 50 having a male portion 52 and a female portion 54. The male portion includes a first end 56 having a flange 58, and a second end 60 having a barb 62, although in other embodiments the second end may only include a post. The female portion of the rivet includes a tubular body 63 having first end 64 with an open bore 66, and a second end 68 having a flange 70 and an eyelet 72. FIG. 3*b* shows one embodiment of the rivet with the male portion mated with the female portion, and in this embodiment the rivet is generally straight. In another embodiment, the male and female portions are curved as shown in FIG. 3*c*. The rivet is delivered to the stomach cavity in an open configuration, as shown in FIG. 3*a*, wherein the male and female portions are not attached to one another. Once in a desired position along the inner stomach wall SW, the rivet is transformed into a closed configuration by inserting the second end of the male portion into the open bore of the female portion. To insert the rivet into or through the stomach wall, a portion of the stomach wall may need to be gathered to form a fold F. The stomach tissue may be gathered by a vacuum or with a mechanical device such as with graspers or forceps. As shown in FIG. 4*a*, the rivet may be inserted into the stomach wall without puncturing through all of the layers of the wall, or in another embodiment, the rivet may be inserted through the stomach wall as shown in FIG. 4*b*. In both embodiments, the eyelet of the rivet is positioned within the stomach cavity. It should be noted that the flanges 58 and 70 provide increased surface area to contact the stomach wall, and therefore the rivet is less likely to detach.

Yet another embodiment of the anchor 40 is shown in FIGS. 5*a* through 6*b*. A rivet 74 similar to rivet 50 is shown, and therefore like reference numerals will correspond to like or similar details of the rivet. The rivet 74 does not include an eyelet, and instead, the rivet 74 includes a through-hole 76 that extends through the male portion 52 and the female portion 54. Once the rivet 74 is positioned within or through the stomach wall SW as shown in either FIG. 6*a* or 6*b*, a tensioning member, such as a suture or wire, can be threaded through the through-hole of the rivet.

Figure 7:
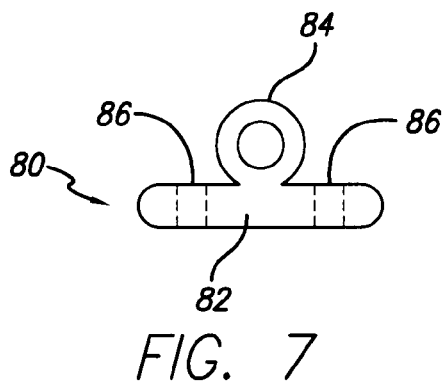
FIG. 7 depicts an anchor.
Figure 8:
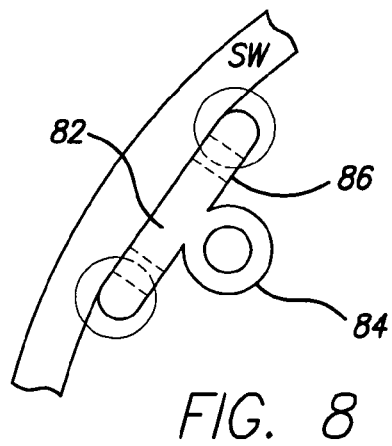
FIG. 8 depicts the anchor of FIG. 7 sutured to the stomach wall.

Another embodiment of the anchor 40 is shown in FIGS. 7 and 8. In this embodiment, an anchor 80 includes a base 82, an eyelet 84 disposed on the base, and at least two through-holes 86 located on opposite sides of the eyelet. In use, the anchor is delivered to the stomach cavity SC and the base of the anchor is placed against the stomach wall SW. Sutures are then threaded through the through-holes and into the stomach wall to attach the anchor as shown in FIG. 8. Multiple anchors may be placed along the stomach wall in a desired pattern, and then a tensioning member threaded through the eyelets of the anchors can be tightened to cinch the anchors together, reducing the volume of the stomach cavity.

All of the anchors disclosed herein can be constructed from titanium, stainless steel, shape-memory alloys, such as nitinol, other biocompatible metal alloys, or various polymers.

A flexible member 88 may also be used when suturing anchors 80 to the stomach wall SW as shown in FIGS. 9*a* and 9*b* to help secure the anchor to the stomach wall by reducing any stress between the anchor and the stomach lining. FIG. 9 shows the surface area of the flexible member being greater than the surface area of the base. Although the flexible member is shown to be round in shape, other shapes, such as oval, square, rectangle, or any polygonal shape may be used. The flexible member may be made from a mesh, or a biocompatible polymer matrix, polyester, nylon, PTFE, collagen matrix, and may further include a metal material formed within or around the mesh to promote healing. When delivering the anchor and the flexible member to the stomach cavity, the flexible member may be integrated with the anchor, pre-attached to the anchor with a suture, or the base of the anchor may be joined to the flexible member with an adhesive. In another embodiment, the flexible member and anchor are delivered separately to the stomach cavity. FIG. 9b shows the anchor and flexible member secured to the stomach wall with two sutures placed through the through-holes 86 and the flexible member into the stomach wall. The flexible member will provide increased surface area to reduce the stress applied to the stomach lining, and if the flexible member is formed of a mesh or mesh-like material, the flexible member could also increase tissue in-growth and/or scarring, resulting in a stronger, more durable attachment. It has also been contemplated that the flexible member could be reinforced, i.e., attached to the stomach tissue via various adhesives.

There are other methods that could also be performed to reduce the stress applied to the stomach wall and to prevent erosion of the tissue/anchor interface. To reduce stress, the number of anchors 40 used in the procedure could be increased. The minimum number of anchors that could be used in this type of procedure would be two, and the maximum number of anchors would be determined by the size of the stomach cavity and the size of the anchor. Also, the "bite" size could also be increased. The term "bite" refers to the amount of tissue gathered or acquired by the anchor to secure itself to the stomach wall. The depth of the "bite" can also be increased to the point of exiting the wall of the stomach. In another embodiment, a flange and/or other stress-reducing element, such as a washer, could be placed on the exterior wall of the stomach. All of these examples would be helpful in reducing the stress on the stomach wall and preventing detachment of the anchor.

Figure 10A:
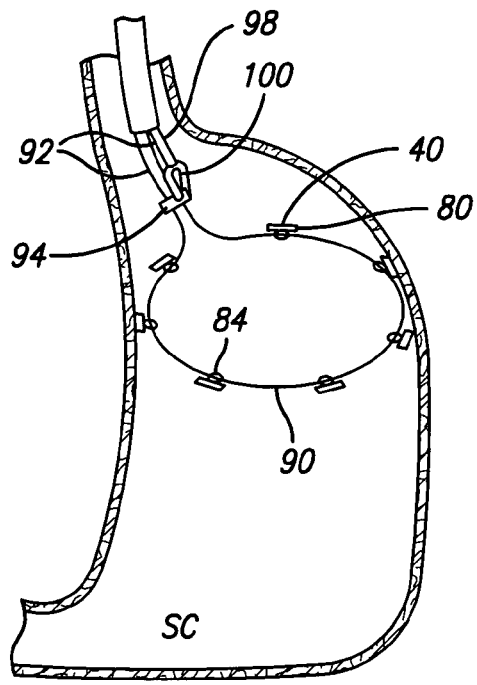
FIG. 10a depicts schematic view of a plurality of anchors attached to the stomach wall.
Figure 12:
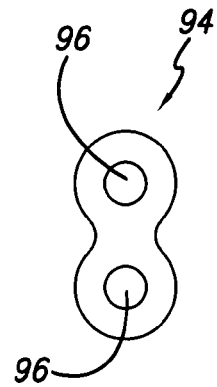
FIG. 12 depicts a cross-sectional view of a clip.
Figure 11A:
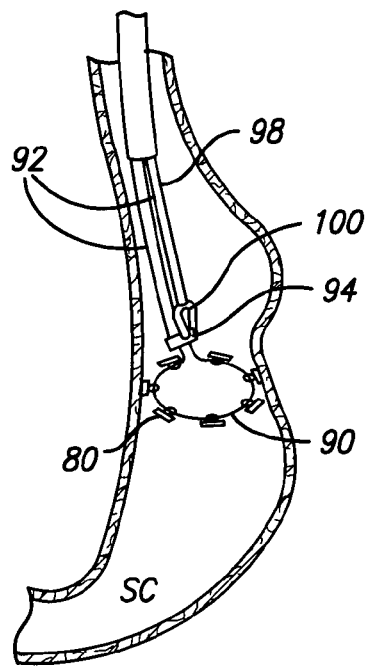
FIG. 11a depicts a schematic view of the anchors being cinched together by tensioning the tensioning member.

In use, multiple anchors 40 are secured around a portion of the stomach cavity SC where the placement of a stricture is desired. The anchors are placed by various devices that will be discussed more below. A partial cross-sectional view of the stomach is shown in FIG. 10 with several anchors attached to the stomach wall. This figure shows the anchors 80 sutured to the stomach wall, although any of the anchors 40, including the staple 42 and the rivets 50 and 74, could be shown because all are used in a similar manner. A tensioning member 90, such as a suture, wire, or zip tie, connects the anchors together by being strung through the eyelets 84 of each anchor. In a case where the rivet 74 is used, the tensioning member would be strung through the through holes 76 of the rivet. The tensioning member may be pre-strung through the eyelets or through-holes of the anchors before each anchor is attached to the stomach wall. FIG. 10a schematically illustrates the entire stomach before the anchors are cinched together. In one embodiment the first anchor to be attached to the stomach wall may be fixedly attached to the tensioning member and the other anchors may be free floating on the tensioning member. After the final anchor is attached, the free end of the tensioning member would be pulled proximally (towards the esophagus) to cinch the anchors and then tied off to the first anchor to secure the tensioning member. In another embodiment shown in FIG. 10a, all of the anchors are free floating on the tensioning member, so that after all of the anchors have been secured around the stomach wall, there are two free ends 92 of the tensioning member that are held together by a clip 94. A cross section of the clip is shown in FIG. 12, the clip is formed of a relatively thin metal, such as stainless steel, carbon, NiTi, tantalum, or other biocompatible metal and includes two lumens 96 that will house the free ends of the tensioning member. One lumen would also be sufficient. To form a stricture by cinching the anchors together, a clamping device 98 having a pair of clamps or pinchers 100 is used to hold the clip in place while the free ends of the tensioning member are pulled proximally. Pulling the tensioning member produces a stricture within the stomach, as shown in FIGS. 11 and 11a. Once a desired tension is achieved producing a stricture of a desired size, the pinchers of the clamping device are activated to crush the clip, thereby closing the lumens of the clip to secure the free ends of the tensioning member. The tensioning member is then cut at a position proximal to the clip, leaving a stricture within the stomach cavity.

The tensioning member 90 should be sufficiently flexible to allow for cinching the anchors together. The tensioning member may be formed from a high-tensil, corrosion-resistant material, e.g., Kevlar fiber, braid or cable; stainless steel wire, braid or cable; polypropylene or other suture materials; or nitinol wire, braid, or cable.

Figure 13:
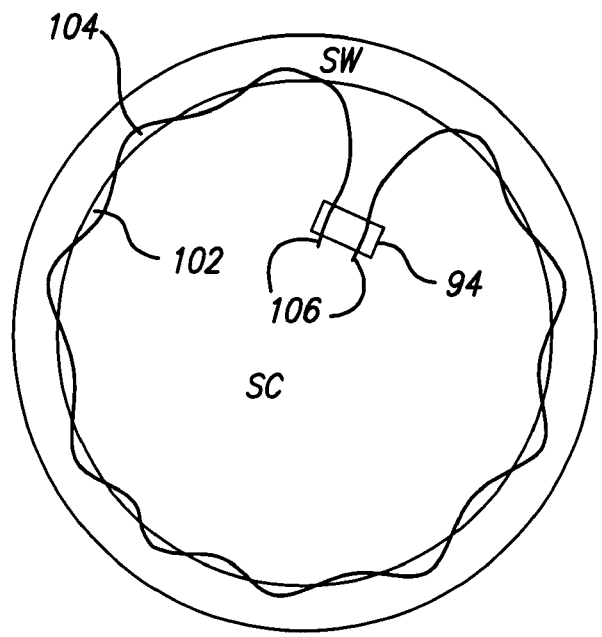
FIG. 13 depicts a cross-sectional view of the stomach cavity with a suture sewn around the stomach wall.
Figure 13A:
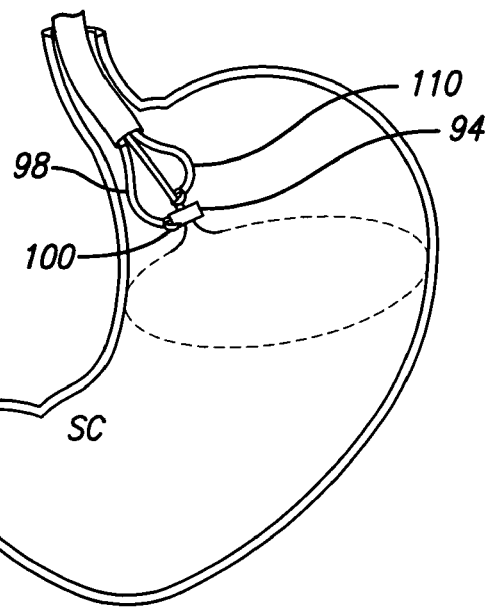
FIG. 13a depicts a schematic view of a stomach cavity with a suture sewn around the stomach wall.
Figure 14:
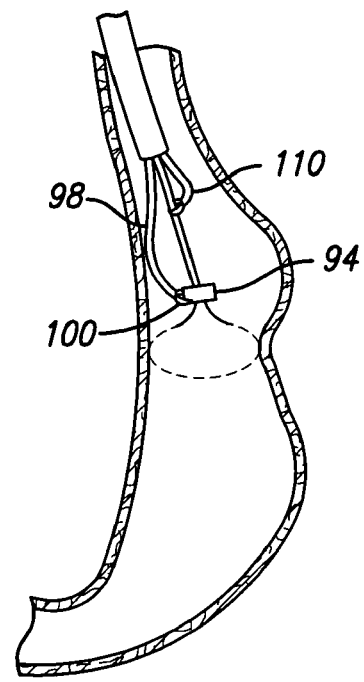
FIG. 14 depicts a schematic view of the stomach cavity of FIG. 13a, with the suture tensioned to form a stricture within the stomach cavity.

Referring now to FIGS. 13 through 14, another embodiment is shown for reducing the volume of the stomach cavity SC. In this embodiment, a device is delivered down the esophagus to the stomach cavity, to allow for in-situ "purse-string" suturing in the stomach. Suturing devices are known in the art, such as the auto-suturing devices from US Surgical. Sutures 102 are used to form a series of "bites" 104 around a portion of the stomach and an internal mechanism is used to pull or cinch the sutures to the desired tension. The suture is then tied off, resulting in a reduction in volume in the stomach cavity. The suture material may include Kevlar, stainless steel wire or cable, nitinol wire or cable, braided Kevlar, and other corrosion-resistant materials. The length of the suture material is such that after an appropriate number of sutures have been applied, two free ends 106 are left in the stomach cavity. In one embodiment, the clip 94 is slid onto the free ends of the suture as shown in FIGS. 13 and 13a. To cinch the sutures, the free ends are pulled proximally with a grasping device 110, while the pinchers 100 of the clamping device 98 are used to hold the clip in a fixed position. Once the desired tension is reached, as shown in FIG. 14, the pinchers of the clamping device are activated to crush the clip, thereby securing the free ends of the suture. The clamping device and grasping device are removed from the stomach cavity, leaving a stricture that reduces the volume of the stomach cavity. It has also been contemplated that the free ends of the suture may be tied together in a knot.

The strictures formed using the tensioning member 90 with anchors 40 or the suture 102 alone could be adjusted for any reason at any time. In one embodiment, and under endoscopic guidance, the tensioning member or suture could be cut, releasing the stricture. A new tensioning member could then be threaded through the eyelets of the anchors 40 or a new suture threaded along the stomach wall, and then tensioned to form a stricture of the desired size. The old tensioning member or suture and clip 94 would have to be removed from the stomach cavity. In another embodiment, the tensioning member could be on a spool or other system such that the tensioning member could be tightened or loosened by rotating the spool in one direction or the other.

Figure 12A:
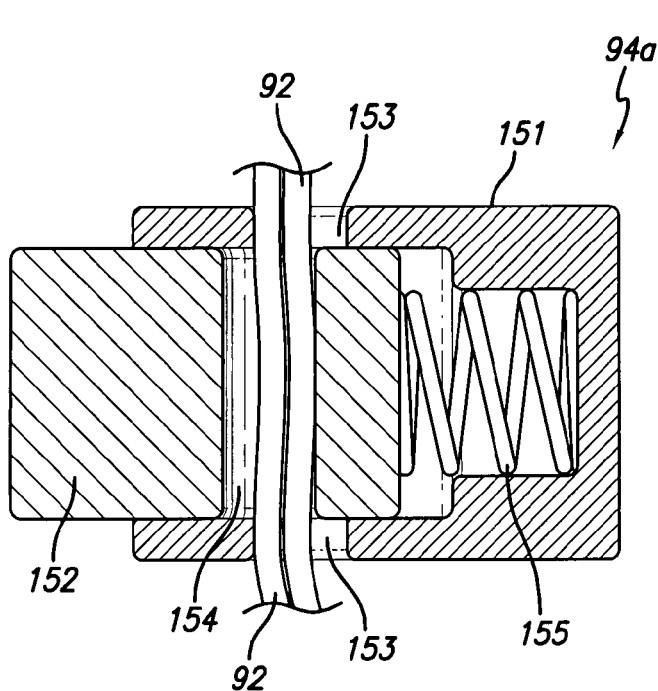
FIG. 12a depicts a cross-sectional view of an adjustable clip.

In another embodiment, the clip could be an adjustable clip 94a, such as the clip disclosed in FIG. 12a. Using the adjustable clip, the tensioning member could be adjusted to increase or decrease the tension of the tensioning member at any time without having to re-string a new tensioning member through the eyelets of the anchors. The adjustable clip includes a housing 151 and a locking member 152 moveable within the housing. A first through-hole 153 is disposed through the housing to accommodate the free end 92 of the tensioning member 90 or suture. The locking member also includes a second through-hole 154, that when lined-up with the first through-hole provides an unrestricted path through the housing and locking member. A spring 155 is disposed within the housing to bias the locking member into a locking position, where the first and second through-holes 153 and 154 are misaligned, thereby locking the free end of the tensioning member within the housing of the adjustable clip. To adjust the tensioning of the tensioning member, the locking member of the adjustable clip would be pushed into the housing against the spring force to align the first and second through-holes into an open configuration to allow the tensioning member to move freely through the adjustable clip. Once the tension of the tensioning member has been adjusted, the locking member would be released, and the force of the spring would bias the locking member, thereby misaligning the through-holes and locking the tensioning member in place. Force could be applied to the locking member with the clamping device 98 described above.

The strictures produced by the anchors 40 and the sutures 102 may be positioned anywhere within the stomach cavity SC between the gastroesophageal junction ("GEJ") and the pylorus, and any number of strictures may be produced to reduce the volume of the stomach. As an example, FIG. 15a schematically shows a loose tensioning member 90 placed around a portion of the stomach cavity. The tensioning member may be secured by anchors to the stomach wall, or may even be the suture 102 discussed above. After the tensioning member is tightened and tied off or secured to a desired diameter, a stricture 112 is formed as shown in FIG. 15b. The volume of the stomach cavity is reduced, and a reservoir R is formed above the stricture in the stomach cavity.

Figure 17A:
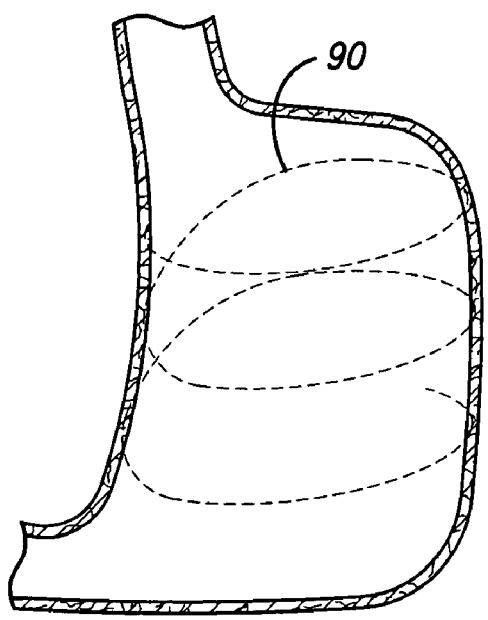
FIG. 17a depicts a schematic view of a stomach cavity with a tensioning member secured to the inner stomach wall in a spiral configuration.
Figure 17B:
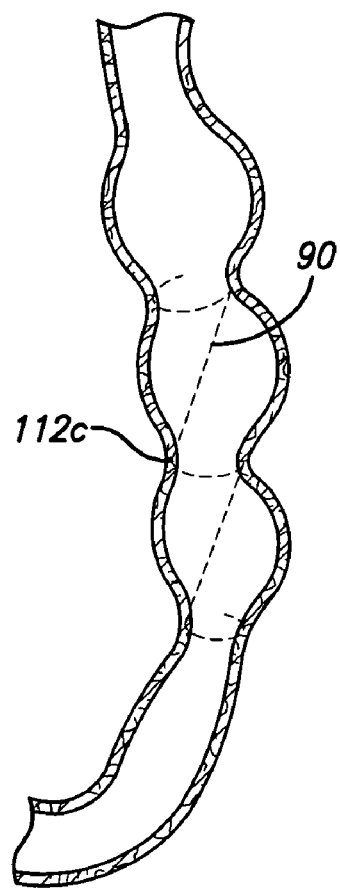
FIG. 17b depicts a schematic view of the tensioning member of FIG. 17a forming a spiral stricture within the stomach cavity.

The length of the stomach cavity SC may be effected by placing multiple strictures within the stomach cavity or by placing a single stricture in a given geometry, such as a spiral. FIG. 16a schematically shows a first tensioning member 90a and a second tensioning member 90b positioned within the stomach cavity, being held with anchors or sutured to the stomach wall. After tightening the tensioning members to a desired diameter, two strictures 112a and 112b are formed as shown in FIG. 16b. The placement of the second stricture further reduces the volume of the stomach cavity. Tensioning members can be tensioned so that the first stricture has a smaller, larger, or the same cross-sectional area as the second stricture. As mentioned, a single stricture can also be used to affect the length of the stomach cavity. FIG. 17a shows a tensioning member 90 spiraled around the stomach cavity, either with anchors or sutured itself. After the tensioning member is tightened to a desired tension, a spiral stricture 112c is formed as shown in FIG. 17b. The spiral configuration may be altered so that the inlet is larger or smaller than the outlet. Also, the tensioning member can be adjusted so that the cross-sectional area of the spiral stricture is variable or generally equal long the length of the stomach cavity.

As previously described, the tensioning member 90 or suture 102 is tensioned or pulled proximally to cinch the anchors 40 or suture in order to form the stricture within the stomach cavity SC. In one embodiment, a calibration device 120 may be used to control the cross-sectional area of the stricture. The calibration device which may include an inflatable balloon 122 (or other inflatable or expanding device) attached to the distal end of a catheter 124. Once the anchors 40 are secured to the stomach wall SW, the calibration device is delivered to the stomach cavity and the balloon is placed in the area of the stomach cavity to be constricted and is inflated to the desired size, as shown in FIGS. 18a and 18b (cross-sectional view). The calibration device would inherently be adjustable for physician control. The tensioning member is then tensioned until the stricture 112 conforms to the calibration device as shown in FIGS. 19a and 19b. The tensioning member is then terminated and the balloon is deflated and removed from the stomach cavity. Use of the calibration device is optional and physicians may prefer to control the size of the stricture themselves without the use of the calibration device.

Referring now to FIGS. 20 through 22, a tissue fixation or stapling device 130 for placing staples 42 within the stomach cavity is shown. The stapling device includes a flexible elongated body 132 having a proximal end 134 and a distal end 136. In one embodiment, the elongated body can be articulated, much like an endoscope. The proximal end includes a handle 138 for maneuvering and activating jaws 140a and 140b of a fixation portion 142. A cartridge of staples can be loaded into jaw 140a of the fixation portion, and in one embodiment, the loaded staples may be pre-strung with a tensioning member 90. In the embodiment shown in FIG. 20, one end of the tensioning member is fixedly attached to the first staple housed in the fixation portion. The other end of the tensioning member is on a spool 144 located at the proximal end of the device in the handle. In another embodiment, the pre-strung tensioning member may not be fixedly attached to the first staple, but looped back inside the delivery device, giving two free ends to join together either by tying a knot or using the clip 94, which would be located within the fixation device. In either embodiment, the staples would be stacked together in the fixation device with the lead staple falling into the delivery mechanism for crimping into the stomach lining. A spring 146 can be located in jaw 140a to advance the next staple into the delivery mechanism. Once the fixation portion of the device is located within the stomach cavity and the distal end is positioned at the desired area for fixation, a lever 148 located on the handle may be squeezed to actuate the jaws 140a and 140b of the fixation portion. Although not shown, the lever actuates the fixation portion using a cable, pulley, and hinges as would be known in the art. Similar to a conventional stapler, the lead staple is ejected from jaw 140a, through the stomach lining and jaw 140b, acting like an anvil, crimps the staple to the stomach lining. After the first staple is secured to the stomach wall, the next staple in succession is advanced by the spring into position for ejection. This process is repeated until all of the desired staples are secured to the stomach wall. In the embodiment where the tensioning member is fixed to the lead staple, a separate device may be used to cut the tensioning member from the spool, or a blade may be incorporated into the stapler device at the distal end to sever the tensioning member after the staples have been cinched together.

In another embodiment shown in FIG. 21, the fixation portion 142 of the stapler device 130 may be actuated using a sheath 150 that is moved distally over the hinged jaws 140a and 140b, thereby actuating the fixation portion and securing a staple into the stomach wall. After a staple is fixed to the stomach wall, the sheath is simply moved in the proximal direction, away from the fixation portion, allowing the jaws 140a and 140b to reset. This process can then be repeated to secure additional staples around a portion of the stomach wall.

An additional embodiment of the distal end 136 of the stapler device 130 is shown in FIG. 22. In this embodiment, the distal end may swivel on a hinge so that the fixation portion 142 is generally perpendicular to the elongated body 132 of the device. It may be beneficial for the anchors to be placed at a angle to the axis of the delivery system.

It may also be advantageous to use a vacuum in conjunction with the delivery device 130. The vacuum could be integrated into the device itself, or could be a separate tube positioned along the device. The vacuum would acquire a portion or "bite" of the stomach wall that could provide a solid foundation for fixing the anchor to the tissue.

During the procedure for placing anchors along the stomach lining, visualization is important and may be accomplished by using an endoscope. In one embodiment, the endoscope connects to the delivery device, for example by a snap fit, so that a standard endoscope may be used. If the standard endoscope is steerable, the elongated body of the delivery device will be sufficiently flexible or articulated near the distal end to allow for the endoscope to position the anchors. In a situation where the endoscope is not steerable, the delivery device will be articulated to allow for placement of the anchors. It also has been contemplated that fiber optics may be used to minimize the overall profile of the device.

An alternative anchor 180 is shown in FIGS. 23a through 23c. Anchor includes a post 182 having a distal end 184 and a proximal end 186. The distal end includes a sharp tip 188 for piercing through the stomach tissue, and the proximal end includes a flange 190 and an eyelet 192. In one embodiment, at least the post is formed of a shape memory alloy, such as nitinol, so that when the post is inserted into the stomach tissue, a lock portion 194 forms near the distal end of the post to secure the anchor into the tissue. In another embodiment, the lock portion is activated mechanically similar to a molly-bolt. As shown in FIG. 23c, the anchor may be fixed to the stomach wall by securing the anchor through a fold F in the stomach lining.

Yet more embodiments of anchors are shown in FIGS. 24a through 24c, and like reference numerals are used for similar details. The anchors of this embodiment are similar to fish hooks. In FIG. 24a, a straight barb anchor 200 is shown, having a post 202 with a distal end 204 and a proximal end 206. The distal end includes a barb 208 and the proximal end includes an eyelet 210. FIG. 24b shows a dual barb hook 212 having two hooks 214, each with a barb at its tip. A triple barb hook 216 is shown in FIG. 24c, and includes three hooks. Although not shown, another embodiment would be a single barb hook. These anchors could be made of a metal alloy such as stainless steel, nitinol, or other spring-like or superelastic material.

FIGS. 24d through 24f depict similar anchors to those shown in FIGS. 24a through 24c, except that the anchors in FIGS. 24d through 24f include a flange 218 at the proximal end 206 of the post 202. Also, the anchors of FIGS. 24d through 24f include a through-hole 219 bored through the flange. A straight barb anchor 200a is shown in FIG. 24d, a dual barb hook 212a is shown in FIG. 24e, and a triple barb hook 216a is shown in FIG. 24f.

Figures 25, 26, 27A:
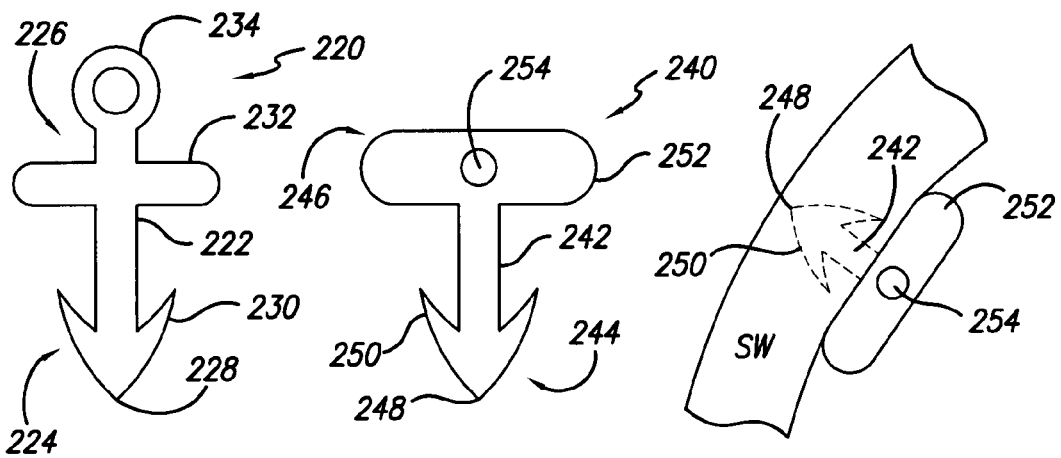
FIG. 25 depicts another embodiment of an anchor.
FIG. 26 depicts yet another embodiment of an anchor.
FIGS. 27a through 27c depict varying sizes of the anchor of FIG. 26 attached to the stomach wall.
Figures 27B, 27C:
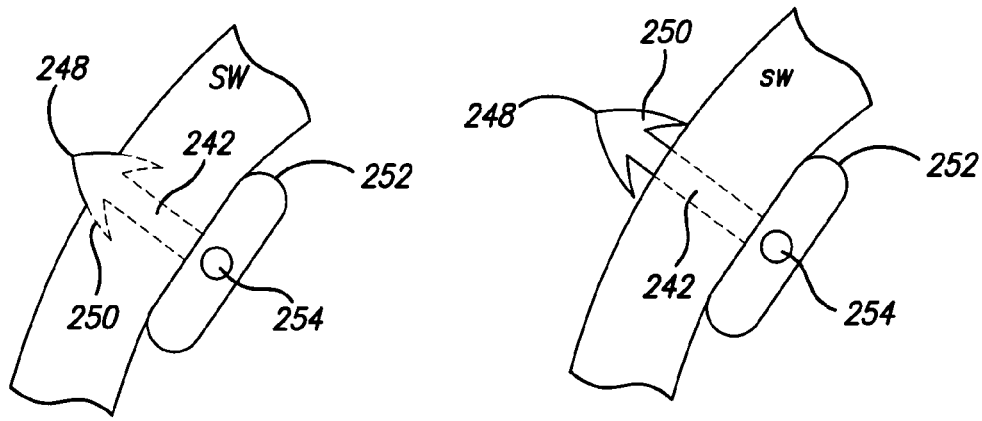

Another embodiment of an anchor 220 is shown in FIG. 25. This anchor includes a post 222 having a distal end 224 and a proximal end 226. The distal end includes a sharp tip 228 and at least one barb 230 (two barbs are preferred) for piercing through the stomach tissue and securing to the stomach tissue. The proximal end includes a flange 232 and an eyelet 234. Referring now to FIG. 26, another anchor 240 is shown having a post 242 with a distal end 244 and a proximal end 246. Similar to anchor 220, the distal end includes a sharp tip 248 and at least one barb 250 (two barbs are preferred) for piercing through the stomach tissue and securing to the stomach tissue. The proximal end includes a flange 252 with a through hole 254 that runs perpendicular to the longitudinal axis of the flange. The posts 222 and 242 of these two anchors 220 and 250 can have varying lengths so that they pierce into the stomach tissue at a certain distance. FIGS. 27a through 27c show the anchor 250 having a post with varying lengths, and the anchor 220 would pierce the stomach wall SW in a similar manner. FIG. 27a shows the anchor with a relatively short post so that the sharp tip and barbs are positioned within the stomach wall. FIG. 27b shows the anchor having a post that is slightly longer than the post shown in FIG. 27a, so that the sharp tip of the anchor is pierced through the stomach wall and the barbs are positioned within the stomach wall. As shown in FIG. 27c, a relatively longer post positions the sharp tip and the barbs on the exterior of the stomach wall.

Figures 28, 29:
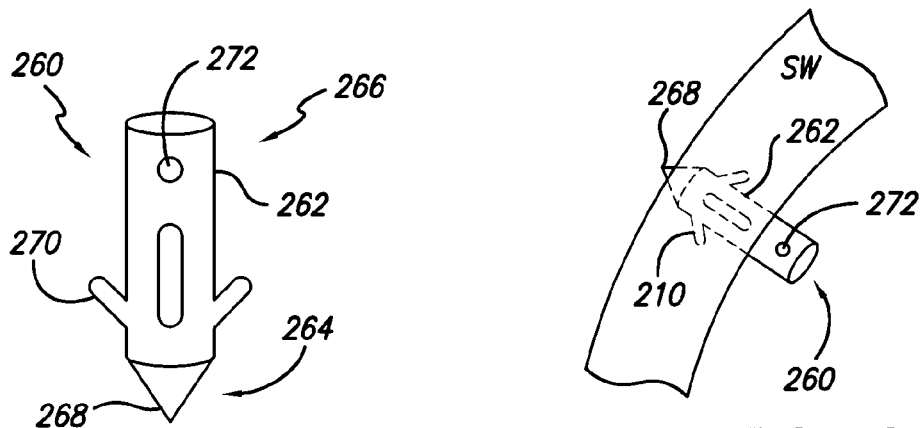
FIGS. 28 and 29 depicts another embodiment of an anchor.

Referring now to FIG. 28, another embodiment of an anchor 260 is shown. The anchor has a generally tubular body 262 with a distal end 264 and a proximal end 266. The distal end includes a sharp tip 268 for piercing the stomach tissue, and barbs 270 are fashioned near the distal end. A through hole 272 is located near the proximal end for joining the anchor to the tensioning member. To manufacture this anchor, its tubular body may be cut from a tubing or stamped and rolled from a sheet. In use, the anchor is pierced into the stomach wall SW so that the barbs are located within the stomach wall and the through hole is located in the interior of the stomach cavity as shown in FIG. 29.

An embodiment of a delivery system 280 will now be discussed that delivers and secures all of the anchors simultaneously to the stomach wall. Delivering all of the anchors simultaneously to the stomach is advantageous because it can provide equal spacing of the anchors, which will help provide an equal amount of stress on each anchor. Also, the time needed to complete the procedure would be reduced by delivering the anchors simultaneously. Referring to FIG. 30, the delivery system is shown to include a delivery sheath 282, which has a distal end 284 and a proximal end (not shown). The delivery sheath houses at least two articulating members or delivery tubes 286 that include a distal end 288 and a proximal end (not shown). The distal end of the articulating members are all attached to an atraumatic tip or nosecone 290, which may be guide wire compatible. An actuating rod 292 is connected to the nosecone and extends through the delivery sheath to the proximal end. As shown in the figures, the articulating members also include a proximal member 294 and a distal member 296, which remain attached to one another by a wire 298. Anchors and the tensioning member may be housed in either the proximal member or the distal member of the delivery tubes. However, it is preferred that the anchors be stored in the proximal member.

In use, the distal end of the delivery shaft 282 is positioned in the stomach cavity through the esophagus under endoscopic guidance, and initially the articulating members or delivery tubes 286 are collapsed within the delivery sheath. It is possible that only the nosecone 290 would be extending from the delivery sheath. Once the system is within the stomach cavity, the delivery sheath is pulled proximally while the delivery tubes are held in position, as shown in FIG. 30. Still fixing the position of the delivery tubes, the actuating rod is pulled proximally to expand the delivery tubes so that an ejection end 300 of the proximal member comes into contact with the stomach wall SW as shown in FIG. 31. A more detailed view of the ejection ends of the delivery tubes is shown in FIG. 32. The anchors 240 are positioned inside the proximal member 294 at the ejection end, and the ejection ends of the proximal members include a slot 302 to allow the anchors to be strung together with the tensioning member 90. As best shown in FIG. 32, plungers or ejectors 304 are disposed within the proximal member of the delivery tubes, and when actuated they push the anchor into the stomach tissue.

All of the anchors in the delivery system 280 can be prestrung together, and in one embodiment the tensioning member may be fixed to a first anchor, pass through each eyelet or through-hole and back through the eyelet of the first anchor, and then up into the delivery sheath 282 to the proximal end. After simultaneously ejecting all of the anchors from the delivery tubes 286 into the stomach wall, the delivery tubes may be removed from the stomach cavity, and the free end of the tensioning member may be tightened at the proximal end of the system to cinch all of the anchors together. Once cinched, the free end of the tensioning member can be secured by tying a knot or other procedures, and then the extra length of the tensioning member can be cut with a separate device. A clip or other slideable member can be advanced over the free end of the tensioning member to a desired position to maintain the stricture formed by the cinched anchors. In another embodiment, all of the anchors in the delivery system may ride freely on the tensioning member. In this configuration, the tensioning member would initiate in the delivery sheath, pass down the sheath and through the eyelets of each anchor, and up into the delivery shaft. The two free ends of the tensioning member could then be clipped together with the clip 94 and then tightened and secured as described above using the clip.

In one embodiment, a vacuum may be applied to the entire stomach cavity through a separate vacuum tube to draw the tissue toward the delivery system 280 and the ejection ends 300 of the delivery tubes 286 to facilitate placement of the anchors. It has been contemplated that the proximal ends of the delivery tubes could be attached to a vacuum source so that before ejecting the anchors, a vacuum can be created at the ejection end of the delivery tube to help in the placement of the anchors.

Another embodiment of a delivery system 320 is shown in FIGS. 33 and 34. The delivery system includes a delivery sheath 322, which has a distal end 324 and a proximal end (not shown). The delivery sheath houses at least two articulating members or delivery tubes 326 that are flexibly or hingedly attached to a distal end 328 of a central rod 330. The delivery tubes each have an attached end 332 and an ejection end 334. At the distal end of the rod is an atraumatic tip such as a nosecone 336. The system also includes a pusher 338 attached to a hollow tube 340 that is disposed over the central rod. Anchors 342 and the tensioning member 90 may be positioned at the ejection end of the delivery tubes as shown in FIG. 35, with the sharp tip 343 of the anchor located out of the delivery. In this embodiment the anchor 342 includes a through-hole 344 in its post 346.

In use, the distal end 324 of the delivery system 320 is delivered down the esophagus to the stomach cavity. As the system is delivered, the plurality of delivery tubes 286 are folded inside the delivery sheath 322 as shown in FIG. 33. Once in position within the stomach cavity, the delivery sheath is pulled proximally while the central rod is held in position to release the delivery tubes. Next, the pusher 338 is pushed distally until it comes into contact with the attached ends 330 of the delivery tubes to expand the delivery tubes into an expanded configuration as shown in FIG. 34. The entire system may then be pulled proximally until sharp tips 343 of the anchors 342 engage the stomach tissue. The anchors are then simultaneously ejected from the delivery tubes and into the stomach wall. It is also possible for the anchors to be ejected one at a time. In one embodiment, the anchors are ejected by a pneumatic pressure. In this embodiment, the central rod can provide a pathway to direct air pressure to the delivery tubes to drive the anchors into the stomach tissue. In another embodiment, the anchors may be ejected by triggering a releasing spring in the delivery tubes. Still in another embodiment, the anchors may be held in the delivery tube by a quick release mechanism, such as a clip or a magnet, and once the anchor is seated in the stomach wall, the anchor is released. Also, similar to the above embodiment, a vacuum can be used to collapse the stomach cavity to facilitate placement of the anchors.

Yet another embodiment of a delivery system 350 is shown in FIG. 36. In this system, a delivery sheath 352, which has a distal end 354 and a proximal end (not shown), houses at least two distal articulating members or distal delivery tubes 356 that are flexibly or hingedly attached to a distal end 358 of a central rod 360. The distal delivery tubes each have an attached end 362 and an ejection end 364. At the distal end of the central rod is an atraumatic tip such as a nosecone 366. The system also includes a pusher 368 attached to a hollow tube 370 that is disposed over the central rod. In this embodiment, at least two proximal articulating member or proximal delivery tubes 372 are also housed within the delivery sheath. The proximal delivery tubes also include an ejection end 374.

In use, the distal end 354 of the delivery system 350 is delivered down the esophagus to the stomach cavity. As the system is delivered, the plurality of delivery tubes 356 and 372 are folded inside the delivery sheath 352. Once in position within the stomach cavity, the delivery sheath is pulled proximally while the central rod is held in position to release the proximal and distal delivery tubes. Next, the pusher 368 is pushed distally until it comes into contact with the attached ends 330 of the distal delivery tubes to expand the distal delivery tubes into an expanded configuration. In one embodiment the proximal delivery tubes are self expanding. The central rod 360 may then be pulled proximally in order to pinch tissue of the stomach wall SW between the proximal and distal delivery tubes as shown in FIG. 36. A fold F of tissue may even be created to place the anchors through. The anchors are then ejected from the ends of the delivery tubes and into the stomach wall.

Many of the anchors described above can be ejected from the distal and proximal delivery tubes 356 and 372 of the delivery system 350. For instance, the male portion 52 of rivet 50 can be loaded into one of the delivery tubes and the female portion 54 of the rivet can be housed in the other delivery tube. Therefore, when the distal delivery tubes are pulled proximally to pinch stomach tissue between the proximal and distal delivery tubes as shown in FIG. 36, the male and female portions of the rivet can be ejected nearly at the same time to mate the male portion with the female portion through the fold of stomach tissue. In another embodiment, the staples 42 could be loaded in one of the delivery tubes (either the proximal or distal tubes) and the other delivery tube could act like an anvil to crimp the arms 46 of the staple into the stomach tissue.

It should be noted that before ejecting any of the anchors from the delivery tubes 356 and 372 of the delivery system 350, a vacuum can be applied to the stomach cavity to collapse the stomach and facilitate the creation of folds F between the delivery tubes. The vacuum can be through the delivery tubes themselves, or a separate vacuum pod can be inserted into the stomach cavity.

Figure 37:
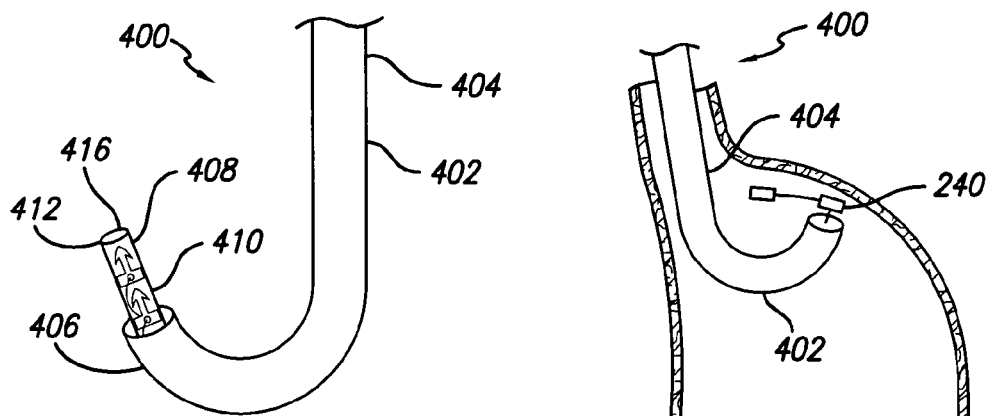
FIGS. 37 through 39 depicts a further embodiment of a device for securing anchors to the stomach wall.
Figure 38:
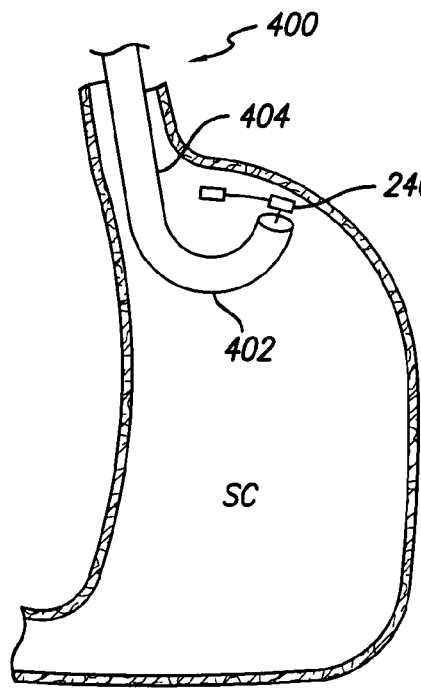
Figure 39:
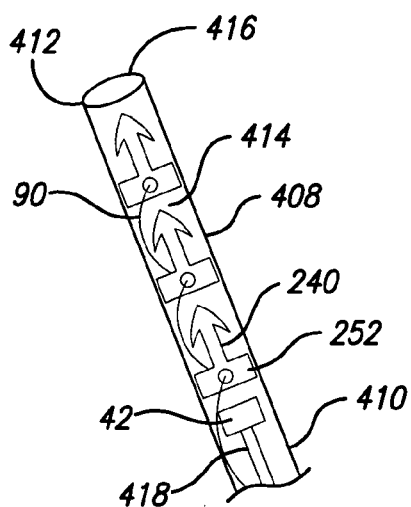

Another embodiment of a delivery system 400 is shown in FIGS. 37 through 39. In this embodiment, the delivery system is incorporated with an articulating endoscope 402, which is known in the art. The endoscope includes an elongated body 404 with the capability of articulation having a proximal end (not shown) and a distal end 406. A delivery tube 408 having a flexible elongated body 410 with a proximal end (not shown) and a distal end 412, and a central lumen 414 extending at least partially between the proximal and distal ends, is disposed within a lumen of the endoscope, as shown in FIG. 37. The delivery tube includes an ejection port 416 at the distal end. The anchors 240 are housed in the central lumen of the delivery tube near the distal end of the delivery tube, and the anchors may pre-strung with the tensioning member 90. Also, a piston 418 is disposed near the distal end of the delivery tube, and has a blunt end 420 that comes into contact with the flange 252 of the last anchor housed in the delivery tube. The piston may be spring loaded or pneumatically driven to drive the anchor into the tissue of the stomach. In use, the distal end of the delivery system is placed within the stomach cavity under endoscopic guidance. The endoscope is then articulated to direct the distal end of the delivery tube toward the portion of the stomach wall where the placement of a stricture is desired. As shown in FIG. 38, the endoscope is articulated so that its distal end is curved to face the stomach wall. Once in position, the piston is actuated to drive the anchor out of the ejection end and into the stomach tissue. After the anchor is secured in the stomach wall, the endoscope can then be twisted or rotated for the placement of the next anchor. The anchors in this embodiment are secured to the stomach sequentially until the last anchor has been deposited in the stomach wall. As previously discussed, the anchors are pre-strung, and when all are delivered to the stomach the tensioning member is tightened and secured, either by tying a knot, using the clip 94 or some other mechanical mechanism.

Figure 40A:
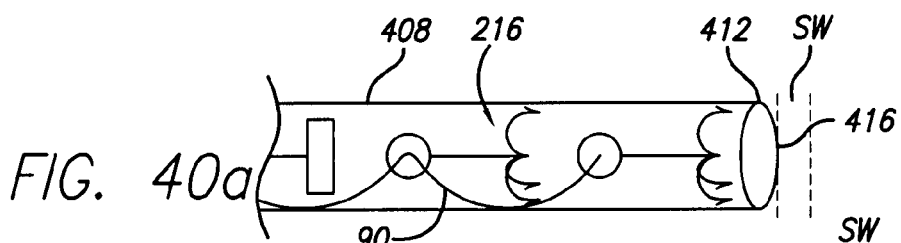
FIGS. 40a through 40c depict a device delivering a three bard hook anchor into tissue.
Figure 40B:
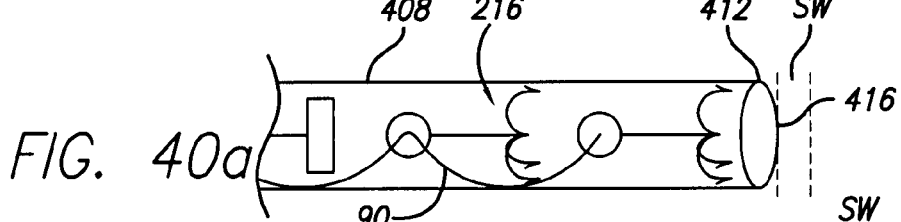
Figure 40C:
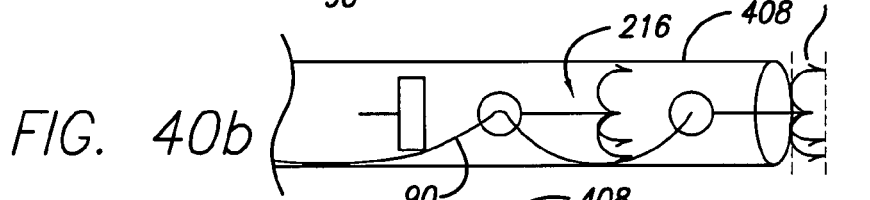

The delivery system 400 could also be used with other types of anchors as well. For instance, FIGS. 40a through 40c depict the delivery tube 408 housing the triple barb hook anchors 216. As mentioned above, the hook anchors are made of a spring steel, nitinol, or other spring-like or superelastic material, so that the hooks and barbs 208 can be bent within the central lumen 414 of the delivery tube. As shown in FIG. 40a, the hooks housed in the delivery tube are bent with the barbs are pointing distally (away from the eyelets), so when the hooks are ejected from the delivery tube, the barbs enter into the stomach wall SW. Referring to FIGS. 40b and 40c, as the hooks are further ejected from the delivery tube, the elastic nature of the hooks forces the hooks and barbs to spring back to its original shape, providing a secure anchor to the stomach wall.

Figure 41:
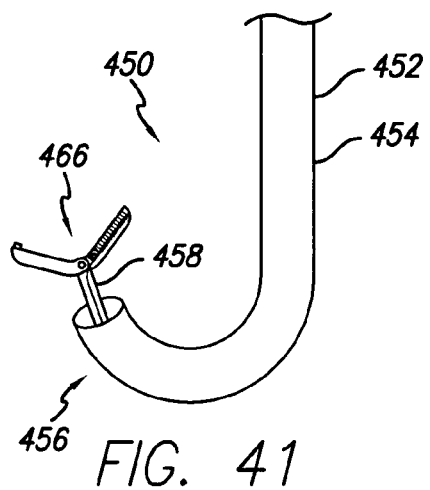
FIGS. 41 and 42 depict another embodiment of a device for delivering anchors to tissue.
Figure 42:
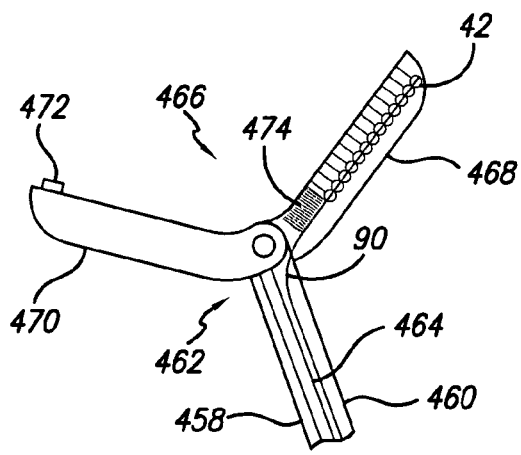
Figure 43:
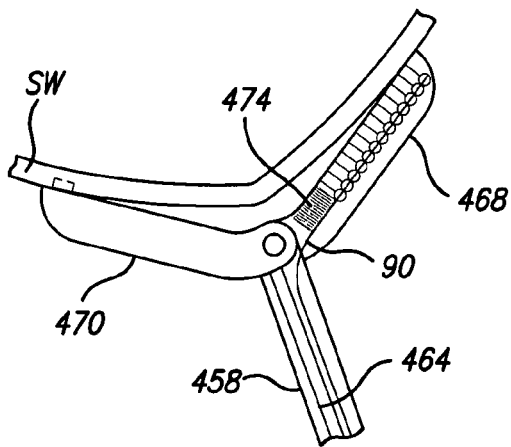
FIGS. 43 through 46 depict the device of FIGS. 41 and 42 delivering a staple to the stomach tissue.
Figure 44:
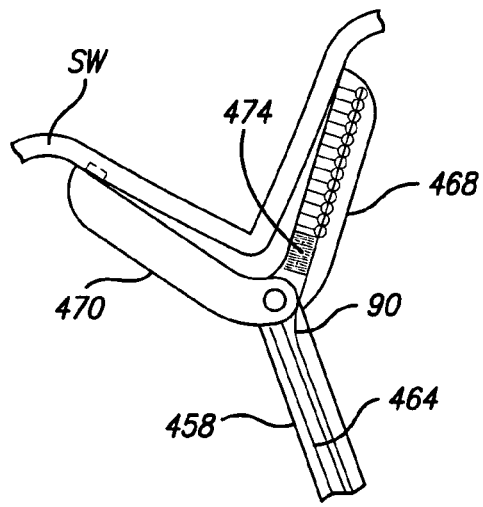
Figure 45:
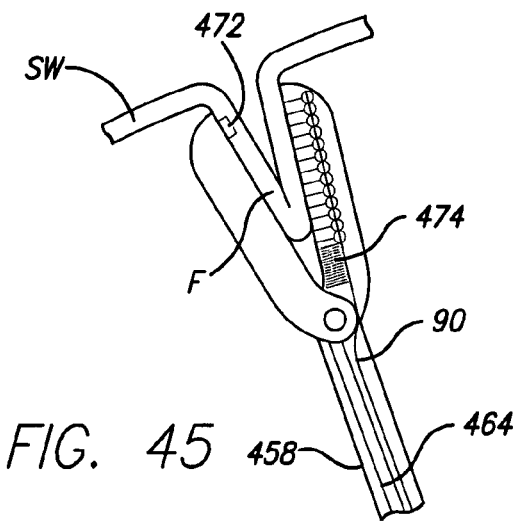
Figure 46:
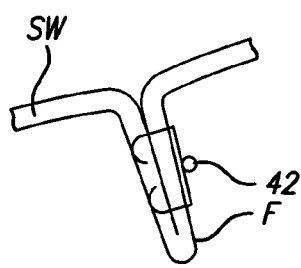

Another embodiment of a delivery system 450 is shown in FIGS. 41 through 45. The delivery system includes an articulating endoscope 452, which is known in the art. The endoscope includes an elongated body 454 with the capability of articulation having a proximal end (not shown) and a distal end 456. A delivery tube 458 having a flexible elongated body 460 with a proximal end (not shown) and a distal end 462, and a central lumen 464 extending at least partially between the proximal and distal ends, is disposed within a lumen of the endoscope, as shown in FIG. 41. At the distal end of the delivery tube is a tissue fixation device 466, that when actuated places anchors within the stomach wall. The tissue fixation device is very similar to the device disclosed above in FIG. 20. In the embodiment shown, a cartridge of staples 42 can be loaded into a first jaw 468 of the device, while a second jaw 470 includes an anvil 472 for crimping the arms of the staples when ejected from the first jaw. As previously discussed with reference to FIG. 20, the loaded staples may be pre-strung with a tensioning member 90. The staples are stacked together in the fixation device with the lead staple falling into the delivery mechanism for crimping into the stomach lining. A spring 474 can be located in the first jaw to advance the next staple into the delivery mechanism. In use, the distal end of the delivery system is positioned within the stomach, and the endoscope is articulated so that the fixation device comes in contact with the stomach wall. In one embodiment, a vacuum may be applied to the central lumen of the delivery tube to facilitate engaging the stomach tissue. Referring to FIG. 43, the first and second jaws of the tissue fixation device can be opened, to bring the distal end of the delivery tube closer to the stomach tissue. The vacuum can then be applied through the central lumen of the delivery tube to grasp onto the desired region of tissue to place an anchor. The jaws can then be actuated to begin closing as shown in FIGS. 44 and 45. As the jaws close, the tissue of the stomach wall SW is still being held by the vacuum pressure, thereby creating a fold F to place the anchor through. To help facilitate in forming the fold, the inside surfaces of the jaws 468 and 470 can be roughed or can include a material that will stick to or grasp onto the stomach tissue without slipping. When the jaws close, a staple 42 is ejected from the first jaw, through the tissue fold, where the anvil of the second jaw crimps the staple in place. After the first staple is secured to the stomach wall, the next staple in secession is advanced by the spring into position for ejection. This process is repeated until all of the desired staples are secured to the stomach wall. FIG. 46. depicts a staple that was placed by the delivery device in the fold of the stomach wall.

Figure 47:
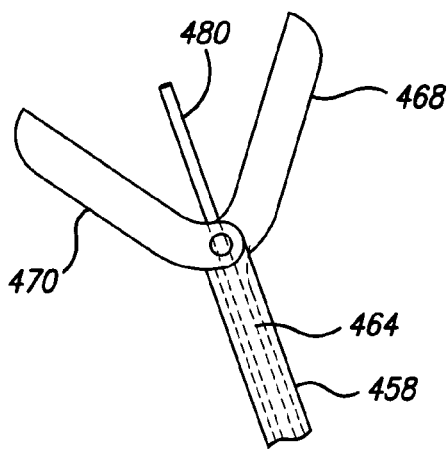
FIG. 47 depicts an alternative embodiment of the delivery device shown in FIGS. 41 and 42.
Figure 48:
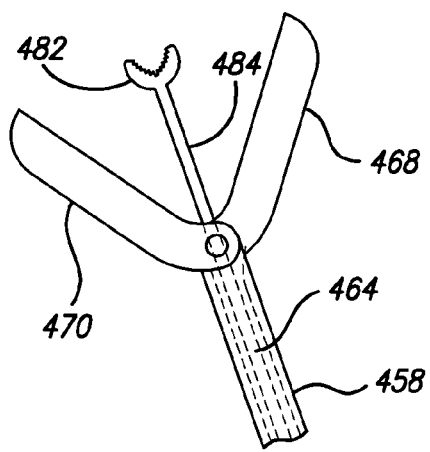
FIG. 48 depicts another alternative embodiment of the delivery device shown in FIGS. 41 and 42.

An alternative embodiment of the delivery device 450 is shown in FIG. 47, wherein a vacuum tube 480 is slidably positioned within the central lumen 464 of the delivery tube 458. After the distal end of the delivery device is positioned within the stomach, and the endoscope is articulated so the tissue fixation device is pointed in the direction of the region of the stomach wall, the vacuum tube can be slide distally until it comes into contact with the stomach wall. A vacuum is then applied through the vacuum tube, allowing the vacuum tube to grasp onto a portion of the stomach wall. The vacuum tube can then be pulled proximally bringing the stomach tissue closer to the distal end of the delivery tube, and thereby helping create a fold to secure an anchor through. FIG. 48 shows another embodiment, wherein graspers 482, such as alligator clips, are disposed at a distal end of a rod 484 that is slidably positioned within the central lumen of the delivery tube. Similar to the vacuum tube embodiment, the rod is extended distally from the delivery tube and the graspers are actuated to grasp onto tissue. The rod is then pulled proximally, bringing the tissue within the graspers with it to facilitate the creation of a fold to secure an anchor through.

Figure 49:
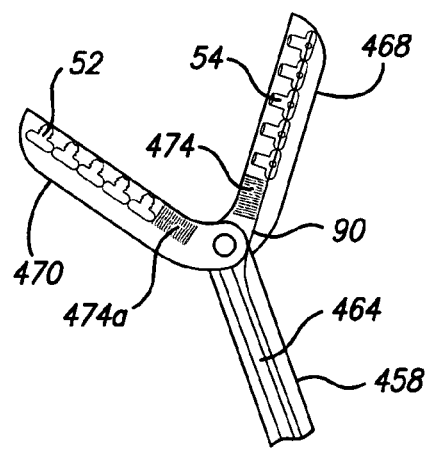
FIG. 49 depicts a delivery device for delivering rivets to tissue.

Although staples 42 are described with the use of the delivery device 450, other anchors may be used as well. For instance, the rivets 50 and 74 may also be used. As shown in FIG. 49, the male portion 52 of the rivet 74 is shown housed in the second jaw 470 of the fixation device 466, and the female portion 54 of the rivet is housed in the first jaw 468 of the fixation device. In this embodiment, the second jaw also includes a spring 474a for advancing the next male portion of the rivet in position for ejection. To place a rivet within the tissue of the stomach, the jaws are closed and the male and female portions of the rivet are ejected at nearly the same time to mate with one another.

Figure 50:
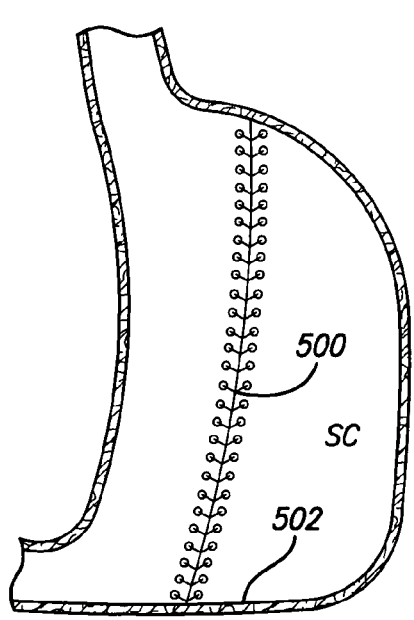
FIGS. 50 and 51 depict a schematic view of a diaphragm positioned within the stomach cavity.
Figure 51:
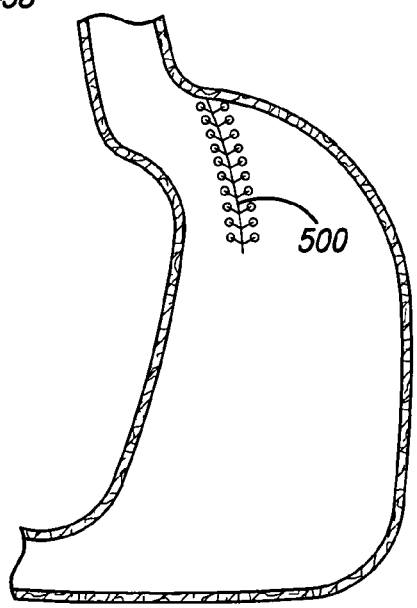

Another embodiment of a device for reducing the stomach volume is a diaphragm 500 that can be deployed within a region of the stomach to divide the stomach cavity into smaller sections. In one embodiment, the diaphragm is placed in a near-vertical orientation to the esophagus and extends along the stomach to the distal portion 502 of the stomach as shown in FIG. 50. Alternatively, the diaphragm could be placed nearly perpendicular to the esophagus or at an angle, such that the cross-sectional area of the food passageway is reduced over a discrete length. In another embodiment, the diaphragm is placed near the gastro esophageal junction ("GEJ"), and substantially parallel to the lesser curve of the stomach as shown in FIG. 51, narrowing the inlet to the stomach, which slows the passage of food from the upper portion of the stomach into the remainder of the stomach.

Figure 52:
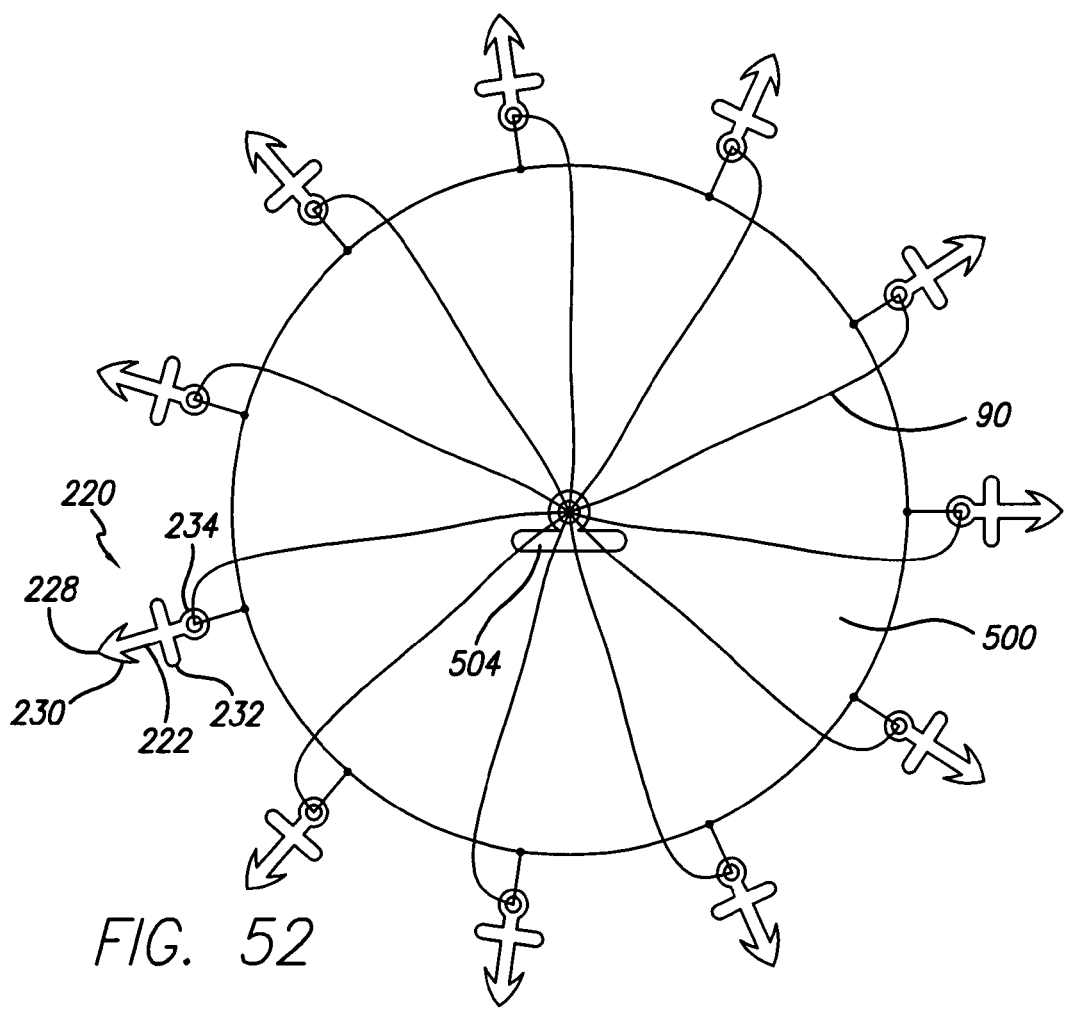
FIG. 52 depicts the diaphragm shown in FIG. 50.

One embodiment of the diaphragm 500 and anchoring mechanism is shown in FIG. 52. The diaphragm is generally circular in shape, although the diaphragm may be generally oval, or any other shape that will span across the stomach cavity. A plurality of anchors 220, although other types of anchors may be used as well, are used to secure the diaphragm to the stomach. Tensioning members 90, such as sutures, are attached to the edge of the diaphragm, pass through the eyelet 234 of the anchors and back to a central eyelet 504 that is attached near the center of the diaphragm. After all of the anchors are secured to the stomach wall, the tensioning members are pulled through the central eyelet and secured to stiffen the diaphragm.

Figure 53:
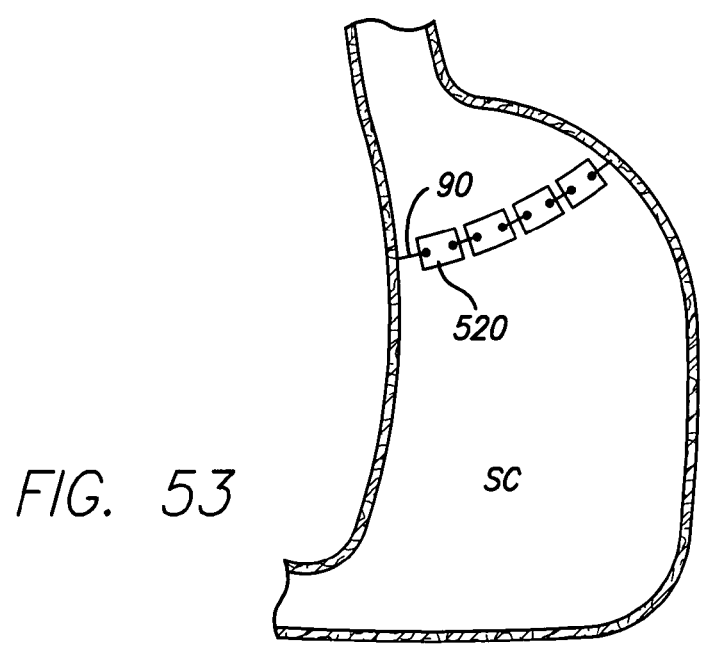
FIG. 53 depicts a schematic view of anchors adhered to the stomach wall.

Another method for reducing the stomach volume is to attach a plurality of anchors 520 to the stomach wall using adhesive. Referring to FIGS. 53 through 56, the anchors will include a base 522 having a bottom surface 524 and a top surface 526, wherein at least one eyelet 528 will be attached to the top surface. The base of the anchor can be manufactured using stainless steel, carbon, NiTi, tantalum, or other biocompatible metal, or could be a composite consisting of a polymer matrix and metal, or just made from a biocompatible polymer. The tensioning member 90 will be strung through the eyelets on each anchor. Once the anchors are fixed to the stomach wall, the tensioning member is tensioned and constrained, forming a stricture in the stomach cavity as shown in FIG. 53. In this manner, the wall of the stomach is not punctured or otherwise damaged and a large anchor surface area may be achieved. The adhesive may be incorporated into the anchor itself or applied via a delivery system. In other embodiments, the anchors may be adhered between two folds of tissue, such that the anchor is sandwiched between the tissue. This may create a more durable bond and may promote tissue ingrowth.

Figure 54:
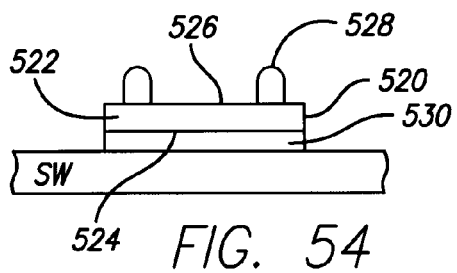
FIGS. 54 through 56 depict an anchor attached to a stomach wall with an adhesive.
Figure 55:
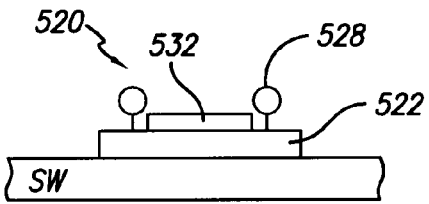
Figure 56:
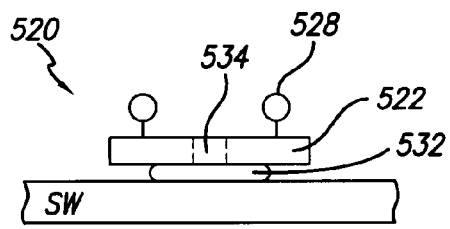

Referring to FIG. 54, an adhesive 530 is disposed on the bottom surface 524 of the anchor 520, and attaches the anchor to the stomach wall SW. The adhesive may include any one of the following, cyanoacrylate tissue adhesive such as Cyanoacrylate Ester (Loctite Corporation), UV cure adhesives, adhesive tapes or felts, adhesive foam, or other substrates, including tissue or collagen substrates modified to increase their adherent qualities. In another embodiment, as shown in FIG. 55, an adhesive capsule 532 is disposed on the top surface 526 of the anchor. The bottom surface of the anchor is positioned against the stomach wall, and the adhesive capsule can be puncture, allowing the adhesive to soak through the base 522 of the anchor to bond to the stomach wall. In this embodiment, the adhesive within the adhesive capsule may be selected from the group listed above. Another embodiment places the adhesive capsule on the bottom surface of the anchor as shown in FIG. 56. In this embodiment, the anchor further includes a through-hole 534 that provides a pathway to the adhesive capsule, so that a pin or other sharp instrument can puncture the adhesive capsule.

Figure 58:
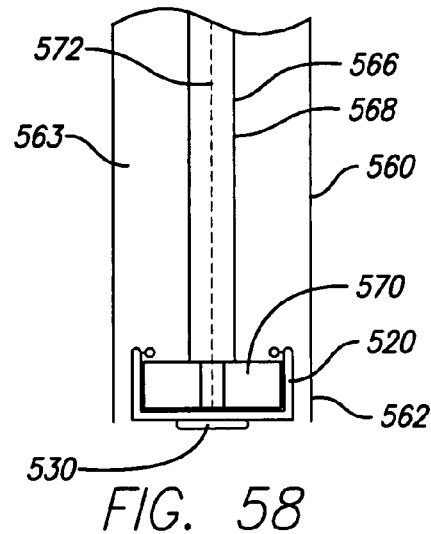
FIGS. 57 and 58 depict a device for delivering the anchors of FIGS. 54 through 56.
Figure 57:
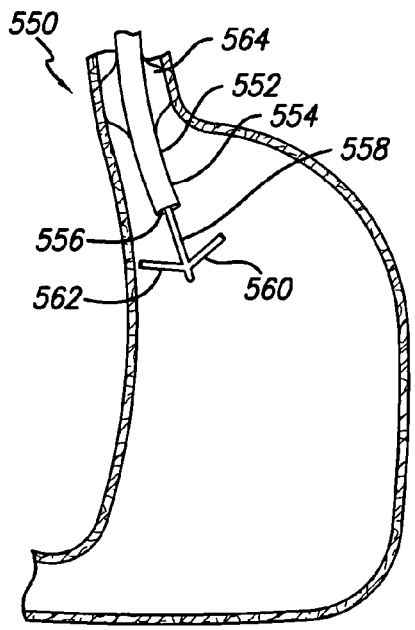

A delivery system 550 for applying the adhesive based anchors 520 is shown in FIGS. 57 and 58. The delivery system includes a delivery sheath 552 with a proximal end (not shown) and a distal end 554, with a central lumen 556 at least partially between the proximal and distal ends. A delivery tube 558 is positioned within the central lumen of the delivery sheath, and includes one or more articulating members 560 with ejection ends 562. The anchors are housed within a lumen 563 in the articulating members and are pushed out of the ejection ends and onto the stomach tissue. Any number of articulating members can be used, and they allow for even spacing of anchors and simultaneous deployment if desired. The system may also include an inflatable balloon 564 located near the distal end of the delivery sheath. During delivery, the balloon can be inflated in the esophagus to facilitate application of positive or negative pressure to the stomach when the anchors are being pushed onto the stomach wall.

A more detailed illustration of the articulating member 560 and anchor 520 is shown in FIG. 58. Positioned within the lumen 563 of the articulating member is a plunger 566 with a rod 568 and a plunger end 570 that abuts against the anchor. Once the system is in position within the stomach, the plunger is moved distally, thereby pushing the anchor out of the ejection end 562 of the articulating member 560 and against the wall of the stomach. The anchor shown includes an adhesive capsule 532, and therefore needs to be punctured to bond the anchor to the stomach wall. To puncture the adhesive capsule, a needle 572 housed within a lumen of the plunger's rod can be moved or actuated in a distal direction to go through the through-hole 534 of the anchor and puncture the adhesive capsule. After the anchor bonds to the stomach wall, the plunger is withdrawn proximally into the articulating member, the delivery tube is withdrawn into the delivery sheath, and the inflatable balloon (if used) is deflated so the system can be removed from the stomach.

Figure 59:
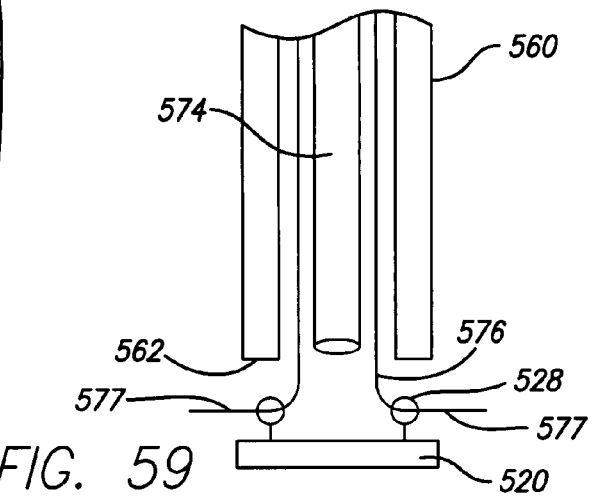
FIG. 59 depicts another embodiment of a device for delivering the anchors of FIGS. 54 through 56.

In an alternative method, the adhesive can be delivered via the delivery system, rather than being incorporated into the anchor 520. FIG. 59 illustrates the end of the articulation member 560, that includes an adhesive tube 574 for dispensing adhesive that will bond the anchor to the stomach wall. Holding wires 576, formed of metal alloys such as nitinol, stainless steel, or superelastic alloy, include shaped tips 577 that are placed through the eyelets 528 of the anchor for holding the anchor in place while the adhesive bonds the anchor to the stomach wall. In use, the anchor is pushed out of the ejection end 562 of the articulating member with the adhesive tube. An adhesive is then released from the adhesive tube that soaks through the anchor and bonds to the stomach wall. Once the anchor is secure, the adhesive tube is drawn back into the articulating member and the holding wires are also retracted into the articulating member.

Figure 60:
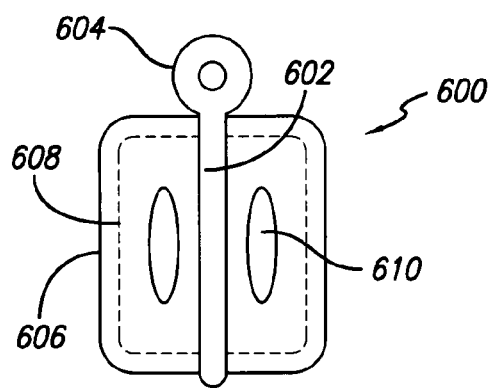
FIG. 60 depicts another embodiment of an anchor.

Another embodiment of an anchor 600 is shown in FIG. 60, and is intended to be placed between folds of stomach tissue. The anchor includes a post 602 having an eyelet 604 at one end and a substrate 606, either mesh or fabric, that is attached to the post. The substrate may include a wire 608, such as a shape-memory wire of nitinol or stainless steel to expand the substrate. Attached to the substrate, preferably on opposite sides of the post, are adhesive capsules 610, that when ruptured will bond the substrate, and hence the anchor in between the fold of stomach tissue. The adhesive may be a moisture activated adhesive, or the adhesive capsule may dissolve quickly to release the adhesive. Once the anchor is secured between a fold of tissue, an additional suture, staple or rivet may be placed through the fold and the substrate of the anchor for added support. As the anchor heals in between the tissue fold, tissue on either side of the substrate will grow into each other, thereby creating a durable attachment.

Figure 61:
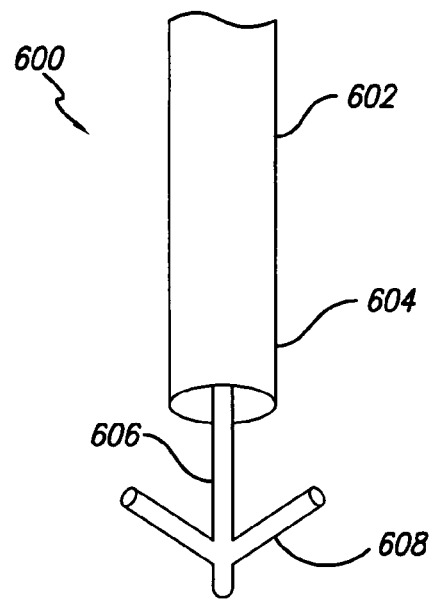
FIGS. 61 and 62 depict a device for delivering the anchor shown in FIG. 60.
Figure 62:
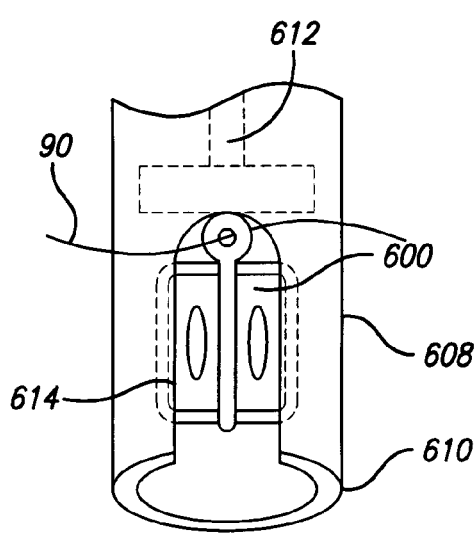
Figure 63:
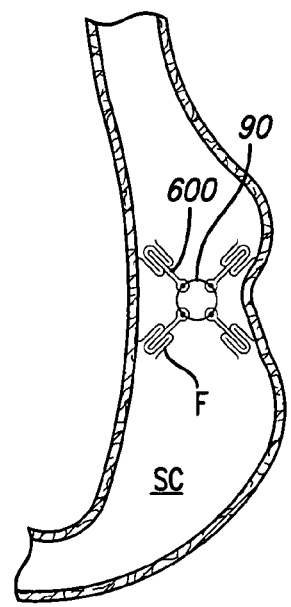
FIG. 63 depicts a schematic view of anchors forming a stricture within the stomach cavity.

FIGS. 61 and 62 illustrate one embodiment of a delivery system for anchors 600. In this delivery system, all of the anchors may be delivered simultaneously. This delivery system is similar to the system disclosed in FIGS. 57 and 58. Referring to FIG. 61, a distal end 604 delivery sheath 602 is shown, with a delivery tube 606 and articulating members 608 extending from the distal end of the sheath. FIG. 62 details an ejection end 610 of the articulating member. A plunger 612 is housed within the articulating member for pushing the anchor out of the ejection end. There is also a slot 614 disposed at the ejection end of the articulating member, so that the tensioning member can be pre-strung through all of the anchors. FIG. 63 schematically illustrates anchors secured between folds of stomach tissue, and the tensioning member tensioned forming a stricture within the stomach cavity.

Figure 64:
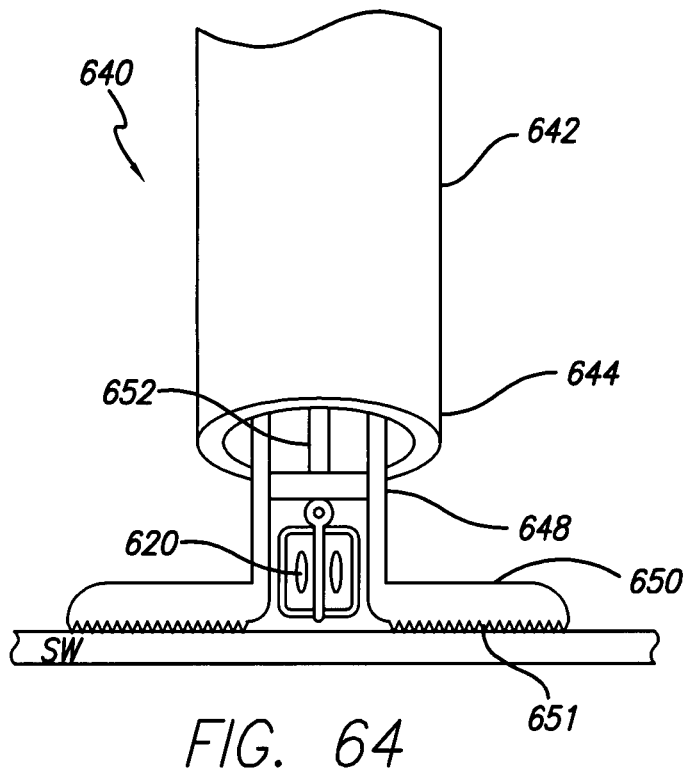
FIGS. 64 and 65 depict another embodiment of a device for delivering the anchor shown in FIG. 60.
Figure 65:
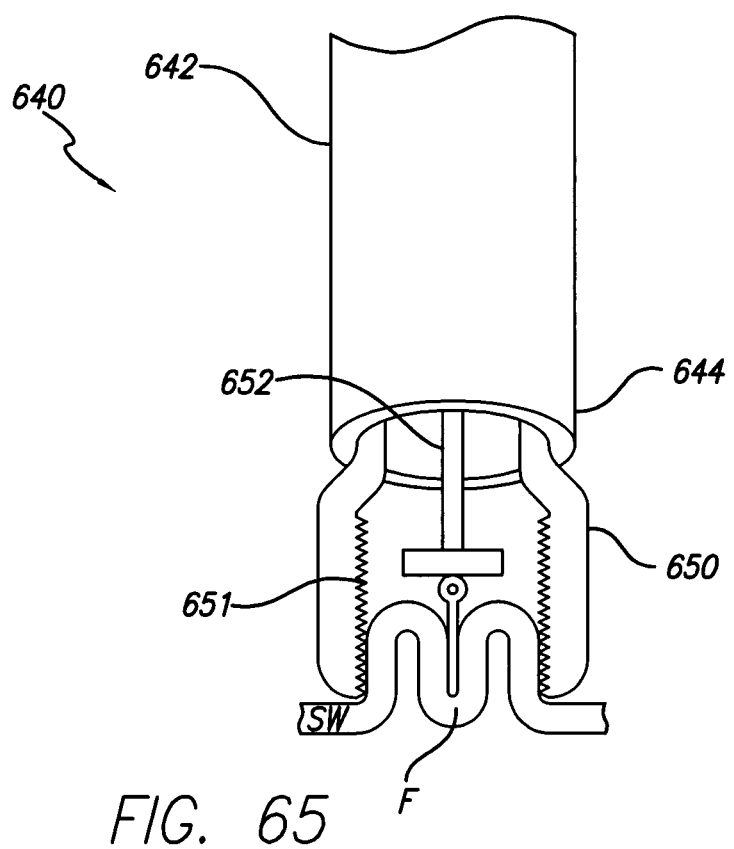

Another embodiment of a delivery system 640 is shown in FIGS. 64 and 65. A delivery sheath 642 having a proximal end (not shown) and a distal end 644, with a central lumen 646 disposed at least partially between the proximal and distal ends. A delivery tube 648 is housed within the central lumen, and the delivery tube includes jaws 650 that move from an open configuration to a closed configuration. The jaws may include a textured surface 651 to better grasp the stomach tissue without slipping. There is also a plunger 652 located within a lumen of the delivery tube. The plunger abuts the anchor 620 which is housed within the delivery tube. In use, the delivery sheath is placed within the stomach and the delivery tube is moved distally out of the delivery sheath, and the jaws of the delivery tube are moved to its open configuration. The anchor is also pushed distally from the delivery tube until it comes into contact with the stomach wall SW. With the plunger holding the anchor in place, the jaws of the delivery tube are moved into its closed configuration as shown in FIG. 65. As the jaws move to the closed configuration, the textured surfaces grip the stomach wall, thereby forming a dual fold F around the anchor. In one embodiment, the jaws close with sufficient force to rupture the adhesive capsules on the anchors. After the anchor is bonded to the fold, the delivery system is removed from the stomach cavity.

Figure 66:
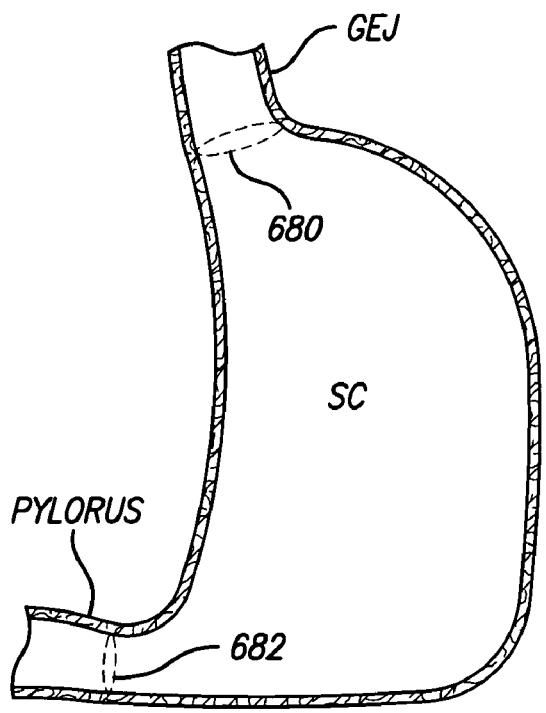
FIG. 66 depicts a first tensioning member secured in the stomach cavity near the GEJ and a second tensioning member secured in the stomach cavity near the pylorus.
Figure 67:
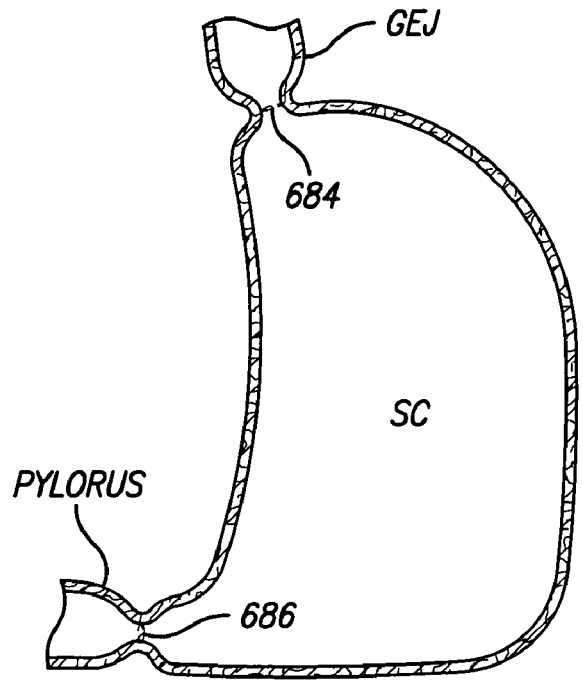
FIG. 67 depicts a first stricture formed near the GEJ and a second stricture formed near the pylorus.

All of the anchors and delivery systems described above place anchors in the stomach wall and cinch them together to form a stricture within the stomach. Multiple strictures may disposed within the stomach. In one embodiment, a first set of anchors 680 is secured to the stomach wall near the GEJ, and a second set of anchors 682 is secured to the stomach wall near the pylorus as shown in FIG. 66. The anchors in the first and second set are all strung together with the tensioning member. In another embodiment, the first and second set of anchors could be replaced with a first suture and a second suture, without the use of anchors. Once the tensioning members are tensioned and fixed, a first stricture 684 and a second stricture 686 are formed within the stomach cavity as shown in FIG. 67. The first stricture restricts food intake, while the second stricture delays gastric emptying. The size of the stoma created by the second stricture could be adjusted so that it is at least as large as the stoma created by the first stricture to prevent obstruction.

Figure 68:
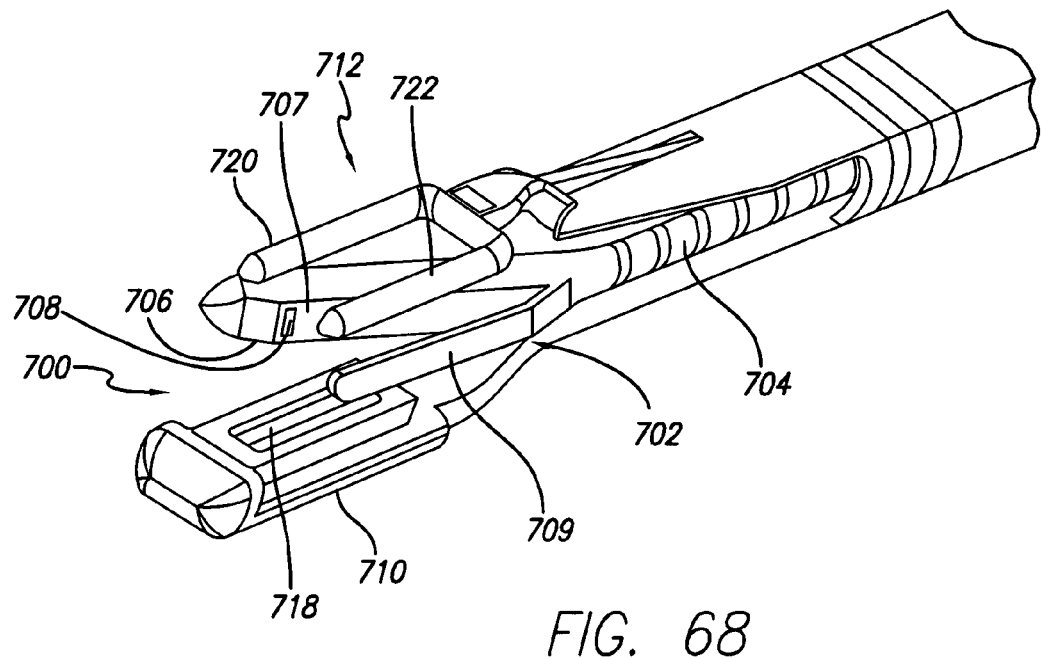
FIG. 68 depicts another device for delivering anchors to a fold of tissue.

Other devices could also be used to place the anchors discussed above in the stomach wall. For instance, the system shown having a folder assembly and a fixation assembly as disclosed in U.S. Ser. No. 10/773,883 ("the '883 application"), titled "Single Fold System For Tissue Approximation And Fixation," could be adopted to place the anchors disclosed herein. The '883 application is hereby incorporated by reference in its entirety. The system disclosed in the '883 application is used to create single fold plications within the stomach cavity with a single anchor or multiple anchors sequentially or simultaneously deployed in an organized fashion. An altered system is illustrated in FIG. 68. The fixation assembly 700 includes a stapler assembly 702 connected via a flexible shaft 704 to a handle (not shown). The stapler assembly includes a staple cartridge 706, that can be adapted to house one or more staples 42 (not shown). In the staple cartridge, the staples may be pre-strung together with a tension member as described above. The staple cartridge can also be adapted to only eject one staple 42 at its distal end, and then advance the next staple into position for ejection, or may simultaneously deploy a row of staples to create a plication in the range of 10-50 mm in length. The face 707 of the staple cartridge is shown in FIG. 68 to only include a single ejection hole 708. An anvil 709 is in apposition to the staple cartridge and is used to provide a staple closure surface when tissue to be affixed is adequately positioned between the staple cartridge and the anvil. To position tissue between the staple cartridge and the anvil, the folder assembly includes a pod member 710 and a tensioning member 712 connected to first and second actuation rods 714 and 716. The pod member may include a vacuum chamber or opening 718 into which tissue may be drawn therewithin. The tensioning member 712 includes tensioning arms 720 and 722 for forming a tissue receiving region between the arms through which tissue may be drawn in through. After tissue is drawn into the pod member and tensioned with the tensioning arms, the stapler assembly can be actuated to place a staple into the fold of tissue created by the folder assembly. This device can then be positioned within the stomach cavity to place another staple into a fold of stomach tissue, or can be repositioned to deploy a row of staples simultaneously to form a longitudinal plication.

Another device that could also be used to place the anchors discussed above in the stomach wall is disclosed in U.S. Ser. No. 10/797,439 ("the '439 application"), titled "Devices And Methods For Placement Of Partitions Within A Hollow Body Organ." The '439 application is hereby incorporated by reference in its entirety. The tissue acquisition and fixation device disclosed in the '439 application is used to create longitudinal dual fold plications within the stomach wall. Slightly altered, the tissue acquisition and fixation device could be used to place the anchors 40 described herein within dual folds. Placing anchors within dual folds could facilitate a secure connection that is less likely to deteriorate for various reasons, including that the plications distribute the load the stomach tissue acquires when it is brought together to narrow the organ which aids healing. Also, the fixation devices may be designed to incorporate at least two layers of stomach wall tissue, and sometimes additional layers including the serosal layer, which can provide greater healing durability once the tissues are in tension in the organ's reduced state. Similar teachings are set forth in U.S. Ser. No. 10/188,547, which is incorporated by reference herein in its entirety. Folds of the present invention may include placing one anchor at a time within a fold, or multiple anchors or staples simultaneously in the form of a longitudinal plication. FIG. 69 illustrates the distal working portion of the tissue acquisition and fixation device 730. The tissue acquisition and fixation device includes a cartridge member 732 and an anvil member 734 that are connected to a tubular member 735. Cartridge member may contain one or more anchors, such as staples 42, which may be actuated via controls located proximally at a handle assembly. A septum or barrier 736 may be removably positioned between the cartridge member and the anvil member. In one embodiment, the septum is replaced with a pledget that would be incorporated into the dual fold. The cartridge member may include a cartridge of staples 42 and an ejection opening 738 for dispensing the staples. The anvil member may include an anvil 740 that corresponds to the ejection opening. Also, both the cartridge and anvil members may include vacuum openings 742 and 744 that are used to acquire tissue. Applying a vacuum to the vacuum openings acquires tissue and the septum or pledget forms a barrier to create a dual fold. If a septum is used, it must be removed before the cartridge and anvil members are actuated to place a staple within the dual fold. However, if a pledget is used in-place of the septum, then the pledget would remain in position between the cartridge and anvil members as a staple or row of staples is placed within the dual fold.

The tissue acquisition and fixation device 730 could also be adapted to place the rivets 50, 74 within a dual fold of tissue. In this embodiment, the cartridge member 732 would be adapted to hold the male portion 52 of the rivet, while the anvil member 734 would be adapted to hold the female portion 54 of the rivet. The anvil member would also include an ejection opening 738a in apposition to the ejection opening 738 on the cartridge member. Both the cartridge member and anvil member would include a spring 746 to advance the next male and female portions in position for ejection. After tissue has been acquired, and the septum is removed, the cartridge and anvil members can be actuated to eject the male and female portions into the dual fold. The male and female portions will mate, securing the dual fold within the stomach cavity.

Figure 68A:
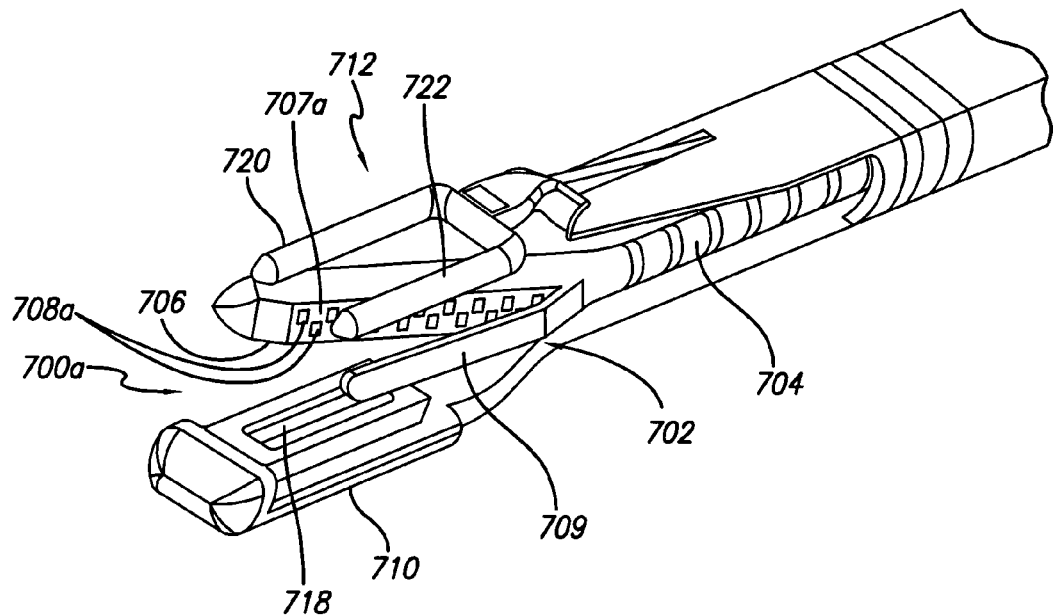
FIG. 68a depicts an alternative embodiment of the device depicted in FIG. 68.

The device as disclosed in the '883 application forms single fold plications within the stomach cavity, and the device as disclosed in the '439 application forms dual fold plications within the stomach cavity. As disclosed in the '883 and '439 applications, the single and dual fold plications are formed by ejecting a plurality of fasteners or staple line into the stomach tissue. The fixation assembly 700a is shown in FIG. 68a with a face 707a include a plurality of ejection holes 708a for dispensing multiple fasteners that will form a staple line to secure the single fold. The tissue acquisition and fixation device 730a is shown in FIG. 69a with the cartridge member 732a including a plurality of ejection openings 738a for dispensing multiple fasteners for forming a staple line to secure the dual fold. Also, the tissue acquisition and fixation device 730a includes a pledget 736a in-place of the septum, and the pledget includes a stiffening member 737, such as a stainless steel wire to expand the pledget. In this embodiment, the pledget 736a will be incorporating into the dual fold. It should be noted, that the device of the '439 may also place a single fold in the event that tissue is only acquired into one vacuum opening. In one embodiment, single or dual folds may be circumferentially placed within the stomach cavity, using one of the devices disclosed in the '883 or '439 applications, and the single or dual folds may then be gathered together to reduce the stomach volume. A tensioning member such as a suture may be used to gather and cinch the folds together, or adjacent folds could be stapled together to reduce the stomach volume. Yet in another embodiment, the folds could be fastened with any of the anchors described above, and then the anchors could be cinched together as previously described.

Figure 71:
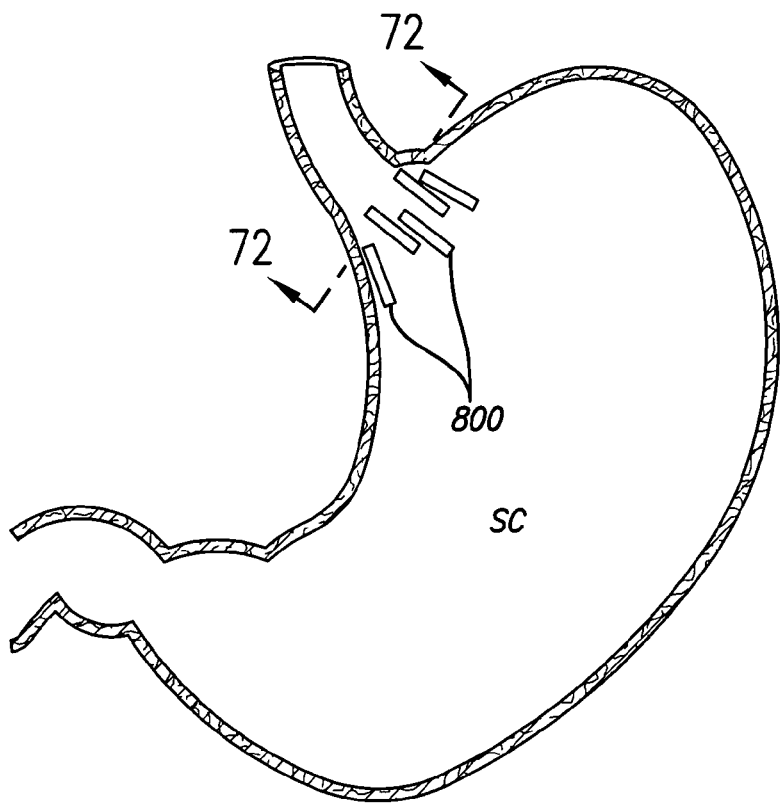
FIG. 71 depicts a schematic view of longitudinal plications disposed in the stomach cavity.
Figure 72:
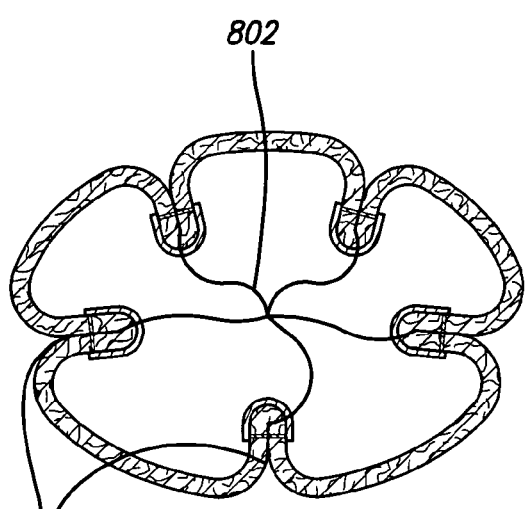
FIG. 72 depicts a cross-sectional view taken along line 72-72 of FIG. 71, wherein the plications are single folds.
Figure 73:
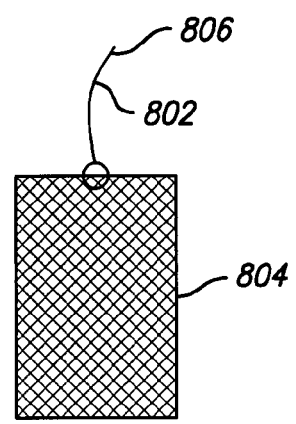
FIG. 73 depicts a pledget.
Figure 74:
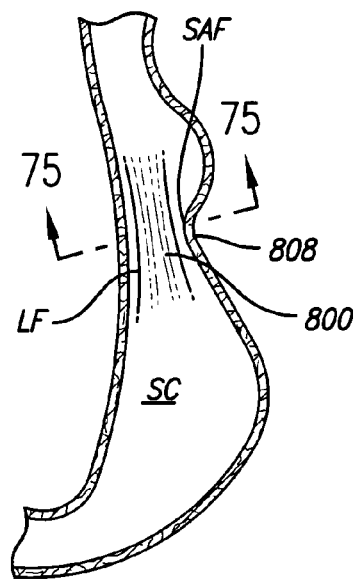
FIG. 74 depicts a schematic view of a stricture created by cinching together plications within the stomach cavity, depicting both radial and longitudinally placed plications.
Figure 75:
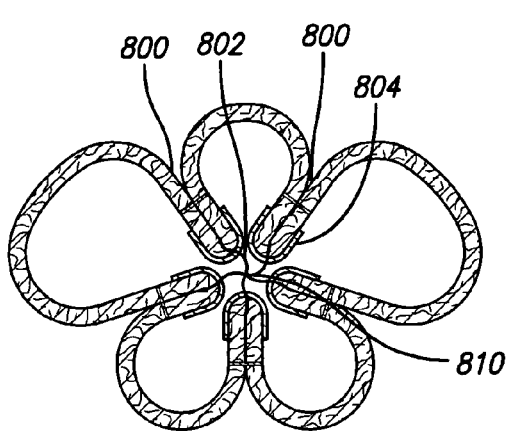
FIG. 75 depicts a cross-sectional view taken along line 75-75 of FIG. 74.

Referring to FIG. 71, a schematic view of a stomach cavity SC is shown with multiple plications 800 placed substantially longitudinally around the circumference of the inner walls of the stomach. FIG. 72 is a cross-section view taken along line 72-72 of FIG. 71, and shows the single fold plications. These single fold plications can be formed using the device disclosed in the '883 application. Gathering elements 802, or sutures, could be attached to the plications or passed through the plications, with the free ends of the gathering elements gathered in the center of the stomach cavity. In one embodiment, a pledget 804, formed of Dacron or mesh, could have the gathering element attached to it. When forming the single fold plications using the device disclosed in the '883 application, the pledget could be placed on the region of tissue that is to be acquired by the tissue fixation device, and then the pledget is fixed to the fold when the plication is formed. The pledget is shown in FIG. 73, with the gathering element attached and the free end 806 of the gathering element unattached. Use of the pledget distributes the load when the gathering element is tensioned. Furthermore, the pledget material may be bioabsorbable such that it absorbs over time once the tissue in the region has healed. Bioerodable or bioabsorbable polymers include polyanhydrides, polyorthoesters, polyesters (such as polylactic acid (PL), polyglycolic acid (PG), polyhydroxybutyric acid, polymalic acid, polyglutamic acid and polylactones) and poly(amino) acids. The free ends of the gathering elements are then tensioned together, thereby pulling the plications together forming a reduction in the stomach volume. A clip 94 as described above can then be crimped around the free ends of the gathering element to secure them. The cinched plications form a stricture 808 that reduces the stomach volume. FIG. 74 illustrates the stricture formed by the cinched folds schematically showing both longitudinal folds LF and shorter single anchor folds SAF. Also, FIG. 75, which is a cross-sectional view of the stricture shows the stoma 810 formed by the cinched folds.

Figure 72A:
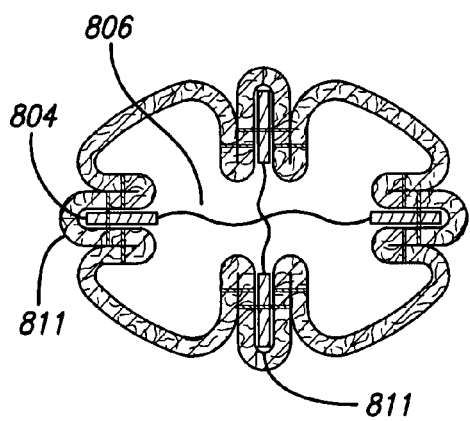
FIG. 72*a* depicts a cross-sectional view of the stomach cavity wherein plications are dual folds.

Dual fold plications 811 placed around the inner surface of the stomach could also be pulled together in a similar manner. The dual fold plications could be created using the tissue acquisition fixation device of the '439 application. The '439 device could include a pledget 804 in place of the optional septum. Therefore, when the tissue is acquired using the vacuum pods of the device, the pledget would be situated in the middle of the two folds, and the cartridge and anvil member would then secure the pledget in the middle of the folds as shown in FIG. 72a. The gathering elements 802 would also be attached to the pledget and the free ends 806 of the gathering elements would be secured together in the middle of the stomach cavity. As with the above embodiment, the free ends would be tensioned together, thereby pulling the dual fold plications together, creating a reduced stomach volume. In some embodiments of the present invention whether a single or multiple anchor(s) and/or fold(s) are placed, the pledget and tensioning member may be optional and the "cinching" step can be simply the act of placing more single or dual folds in the vicinity or over the top of the folds already placed (overstapling), until the stoma or stricture is of such a diameter that the tissue fixation device can no longer be passed into position. In all cases, the desired stoma diameter is between 0.25 cm and 2 cm, for example 1 cm. In these embodiments, the act of acquiring the tissue would be the equivalent to the tensioning element.

Figure 76:
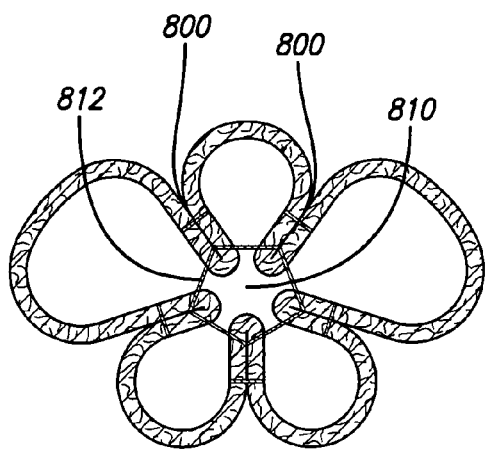
FIG. 76 depicts a cross-sectional view of the stomach cavity where plications are cinched together with staples.

The plications 800 could also be cinched together by stapling or fixing adjacent plications together. FIG. 76 shows a cross-sectional view of the stoma 810 formed by stapling adjacent plications together. In this embodiment, the plications can be re-acquired by a device, such as the device disclosed in the '883 application or the device disclosed in the '439 application, and then fixed together with staples 812. Although all of the plications may be fixed together, the stomach volume would also be reduced by only fixing one adjacent plication. Yet in another embodiment, a single gathering element 802, or suture, could be passed through each plication, and then the free ends of the gathering element would be tensioned to cinch or circumferentially gather the plications. The free ends of the gathering element could then be tied together or crimped together using the clip 94 or other device to secure the gathering element. The resulting stoma would be similar to the one shown in FIG. 76.

In another embodiment, fastening lines 820 can be placed within the stomach cavity to create partitions within a hollow organ such as the stomach, as described in U.S. Ser. No.

Figure 77:
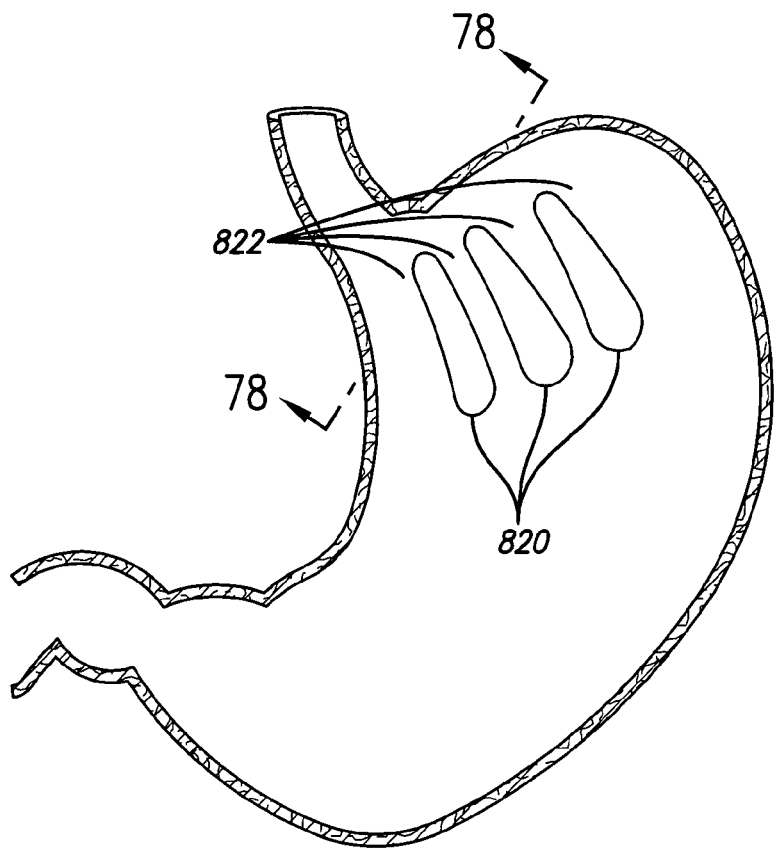
FIG. 77 depicts a schematic view of a stomach cavity with three fastening lines creating lumens within the stomach.
Figure 78:
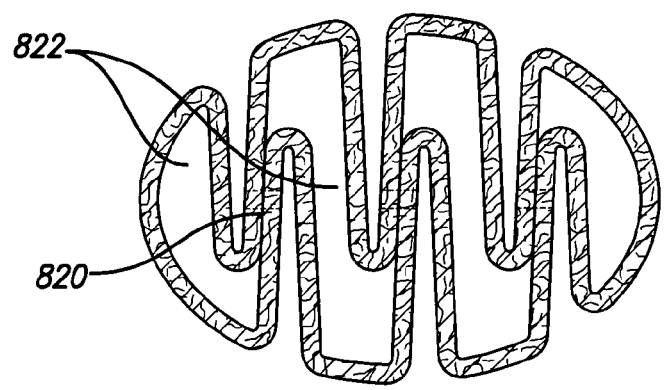
FIG. 78 depicts a cross-sectional view taken along line 78-78 in FIG. 77.
Figure 79:
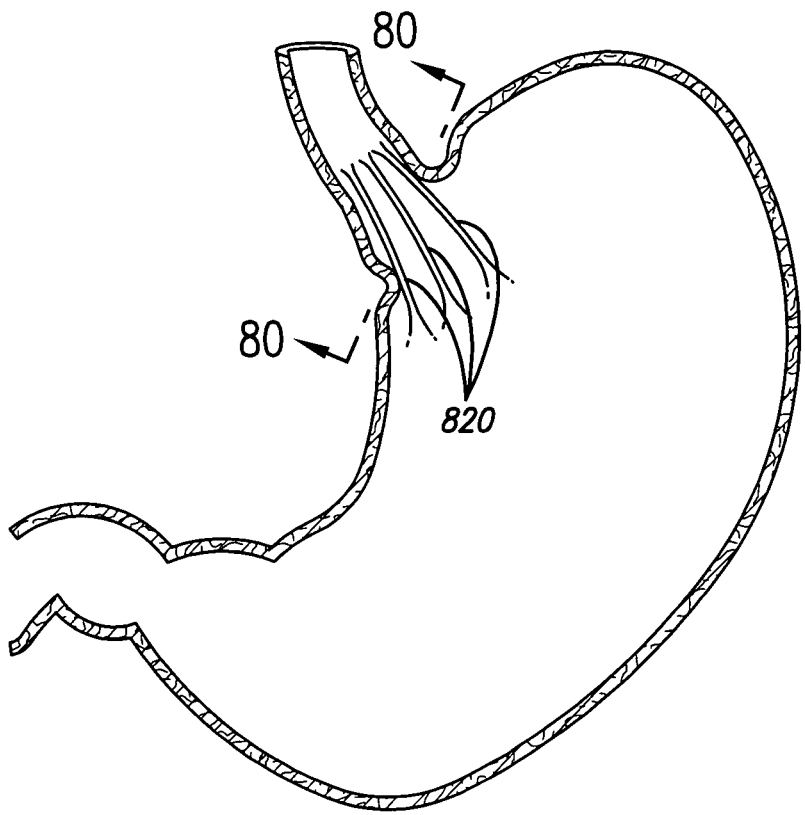
FIG. 79 depicts a schematic view of the stomach cavity shown in FIG. 77 wherein the fastening lines have been cinched together.
Figure 80:
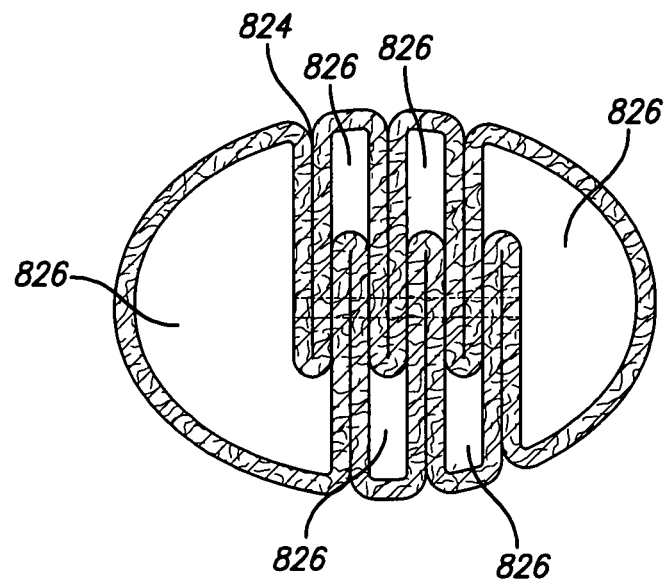
FIG. 80 depicts a cross-sectional view taken along line 80-80 of FIG. 79.

10/188,547 ("the '547 application"), titled "Method And Device For Use issue Approximation And Fixation," which is hereby incorporated by reference in its entirety. The tissue acquisition device described in the '547 application creates these partitions by acquiring and fixing together tissue taken from the posterior wall and anterior wall of the stomach. FIG. 77 illustrates three fastening lines that create four individual lumens 822 through the stomach cavity. A cross-section taken along line 78-78 of FIG. 77 is shown in FIG. 78. To further reduce the volume of the stomach cavity, the partitions created by the fastening lines can be fixed together. In one embodiment, a tensioning member 824, such as a suture, is placed through the fastening lines, perpendicular to the orientation of the partitions as shown in FIG. 78. This restriction creates four or as many as six or more reduced lumens 826 depending on the amount of additional plications placed, or regions tensioned. In another embodiment, staples or other types of anchors may be used to fix the partitions together. In either embodiment, the stomach volume will be reduced.

Figure 81:
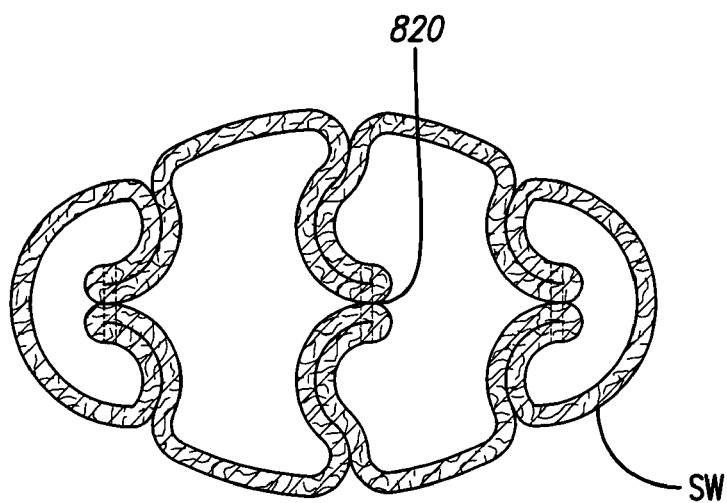
FIG. 81 depicts a cross-sectional view of a stomach cavity with three fastening lines.
Figure 82:
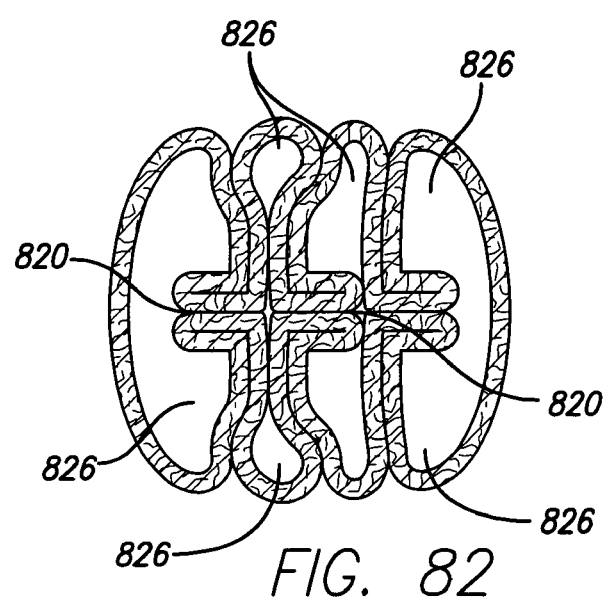
FIG. 82 depicts a cross-sectional view of the stomach cavity shown in FIG. 81 wherein the fastening lines are cinched together.

The fastening lines 820 may also be placed with the tissue acquisition and fixation device disclosed in the '439 application to form the partitions. FIG. 81 shows a cross-sectional view of the partitions formed with the '439 device. These partitions can then be fixed together in a similar manner as described above using a tensioning member 824, such as a suture or staples. This restriction will also create four or as many as six or more reduced lumens 826 as shown in FIG. 82, depending on the amount of additional plications placed, or regions tensioned.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials described herein are intended to define the parameters of the invention, they are by no means limiting and are exemplary embodiments.

We claim:

1. A system for reducing the volume of a stomach cavity, comprising:
   a tubular member having a proximal end and a distal end;
   a tissue acquisition and fixation device disposed at the distal end of the tubular member, the tissue acquisition and fixation device including first and second members movable from an open configuration to a closed configuration to substantially simultaneously create first and second folds of tissue;
   a pledget removably disposed between the first and second members of the tissue acquisition and fixation device, such that the pledget is configured to be positioned between the first and second folds of tissue created by the tissue acquisition and fixation device, the pledget including an elongate, flexible tether having one end attached to the pledget and a free end extending therefrom that is configured to be tensioned to manipulate tissue to which the pledget is attached; and
   an anchor housed within the first member of the tissue acquisition and fixation device, and the anchor being adapted to secure the pledget between the first and second folds of tissue when the tissue acquisition and fixation device moves from the open to the closed configuration.

2. The system of claim 1, wherein the first and second members of the tissue acquisition and fixation device include vacuum pods for acquiring tissue within the stomach cavity.

3. The system of claim 1, wherein the pledget includes a substrate formed of Dacron, mesh, or fabric.

4. The system of claim 3, wherein the pledget includes a wire attached to the substrate for expanding the substrate.

5. The system of claim 1, wherein the anchor is a staple or rivet.

6. The system of claim 1, wherein multiple anchors are housed within the first member of the tissue acquisition and fixation device.

7. The system of claim 1, wherein the tissue acquisition and fixation device is adapted to secures multiple pledgets within multiple folds of tissue and the multiple pledgets are adapted for being cinched together to create a stricture within the stomach cavity.

8. The system of claim 7, wherein the multiple pledgets each comprise an elongate, flexible tether such that the tethers are adapted to be tensioned together to create a stricture within the stomach cavity.

9. The system of claim 1, wherein the pledget is bioabsorbable.

* * * * *